(12) United States Patent
Brown et al.

(10) Patent No.: US 11,871,952 B2
(45) Date of Patent: Jan. 16, 2024

(54) SURGICAL DEVICE WITH INCORPORATED TISSUE EXTRACTION

(71) Applicant: Covidien LP, Mansfield, MA (US)

(72) Inventors: Ashlie M. Brown, Denver, CO (US); Tejas S. Inamdar, San Francisco, CA (US); Bradley R. Heil, Reston, VA (US); Subhrangshu Datta, Arlington, MA (US); Jeremy A. Van Hill, Somerville, MA (US); Sylvain B. Jamais, Ely (GB); Martin J. Dinnage, Ely (GB); Derek W. Henderson, Cottenham Cambs (GB)

(73) Assignee: Covidien LP, Mansfield, MA (US)

( * ) Notice: Subject to any disclaimer, the term of this patent is extended or adjusted under 35 U.S.C. 154(b) by 248 days.

(21) Appl. No.: 16/860,627

(22) Filed: Apr. 28, 2020

(65) Prior Publication Data
US 2020/0253628 A1     Aug. 13, 2020

Related U.S. Application Data

(63) Continuation of application No. 15/535,136, filed as application No. PCT/US2015/066111 on Dec. 16, 2015, now Pat. No. 10,631,889.
(Continued)

(51) Int. Cl.
*A61B 17/32*     (2006.01)
*A61B 17/00*     (2006.01)
*A61B 17/42*     (2006.01)

(52) U.S. Cl.
CPC ...... *A61B 17/32002* (2013.01); *A61B 2017/0023* (2013.01); *A61B 2017/0046* (2013.01);
(Continued)

(58) Field of Classification Search
CPC ...... A61B 17/32002; A61B 2017/0023; A61B 2017/0046; A61B 2017/320024; A61B 2017/4216; A61B 2217/005
See application file for complete search history.

(56) References Cited

U.S. PATENT DOCUMENTS

| 1,585,934 A | 5/1926 | Muir |
| 1,666,332 A | 4/1928 | Hirsch |

(Continued)

FOREIGN PATENT DOCUMENTS

| CN | 102961173 A | 3/2013 |
| WO | 2010089777 A2 | 8/2010 |

OTHER PUBLICATIONS

International Search Report issued in corresponding International Application No. PCT/US2015/066111 dated Jun. 23, 2016, 4 pages.
(Continued)

*Primary Examiner* — Sarah A Long
(74) *Attorney, Agent, or Firm* — Carter, DeLuca & Farrell LLP

(57) ABSTRACT

Systems and methods discussed herein relate to surgical systems including tissue resecting devices where the handset has a disposable portion detachably coupled to a reusable portion. The reusable portion may be a housing where a motor and electronics are stored that may be used to drive a shaft inserted into the disposable portion. The shaft may be coupled to a fluid pathway through the disposable portion that is fluidly isolated from the reusable section. After use, the disposable section is detached from the reusable section and disposed, and the reusable section may be cleaned and sterilized, or may be cleaned only.

14 Claims, 18 Drawing Sheets

Related U.S. Application Data

(60) Provisional application No. 62/092,686, filed on Dec. 16, 2014, provisional application No. 62/092,698, filed on Dec. 16, 2014.

(52) U.S. Cl.
CPC ............ *A61B 2017/320024* (2013.01); *A61B 2017/4216* (2013.01); *A61B 2217/005* (2013.01)

(56) References Cited

U.S. PATENT DOCUMENTS

| | | |
|---|---|---|
| 1,831,786 A | 11/1931 | Duncan |
| 2,708,437 A | 5/1955 | Hutchins |
| 3,297,022 A | 1/1967 | Wallace |
| 3,686,706 A | 8/1972 | Finley |
| 3,734,099 A | 5/1973 | Bender et al. |
| 3,791,379 A | 2/1974 | Storz |
| 3,812,855 A | 5/1974 | Banko |
| 3,835,842 A | 9/1974 | Iglesias |
| 3,850,162 A | 11/1974 | Iglesias |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,284 A | 7/1986 | Arakawa et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Thimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk-Burleson et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,195,541 A | 3/1993 | Obenchain |
| 5,226,910 A | 7/1993 | Kajiyama et al. |
| 5,244,459 A | 9/1993 | Hill |
| 5,254,117 A | 10/1993 | Rigby et al. |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Trese et al. |
| 5,312,399 A | 5/1994 | Hakky et al. |
| 5,312,425 A | 5/1994 | Evans et al. |
| 5,312,430 A | 5/1994 | Rosenbluth et al. |
| 5,320,091 A | 6/1994 | Grossi et al. |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,409,453 A | 4/1995 | Lundquist et al. |
| 5,411,513 A | 5/1995 | Ireland et al. |
| 5,421,819 A | 6/1995 | Edwards et al. |
| 5,425,376 A | 6/1995 | Banys et al. |
| 5,429,601 A | 7/1995 | Conley et al. |
| 5,435,805 A | 7/1995 | Edwards et al. |
| 5,443,476 A | 8/1995 | Shapiro |
| 5,449,356 A | 9/1995 | Walbrink et al. |
| 5,456,673 A | 10/1995 | Ziegler et al. |
| 5,456,689 A | 10/1995 | Kresch et al. |
| 5,483,951 A | 1/1996 | Frassica et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,178 A * | 10/1996 | Henley .......... A61B 17/320783 604/22 |
| 5,569,254 A | 10/1996 | Carlson et al. |
| 5,569,284 A | 10/1996 | Young et al. |
| 5,575,756 A | 11/1996 | Karasawa et al. |
| 5,591,187 A | 1/1997 | Dekel |
| 5,601,583 A | 2/1997 | Donahue et al. |
| 5,601,603 A | 2/1997 | Illi |
| 5,602,449 A | 2/1997 | Krause et al. |
| 5,603,332 A | 2/1997 | O'Connor |
| 5,630,798 A | 5/1997 | Beiser et al. |
| 5,649,547 A | 7/1997 | Ritchart et al. |
| 5,669,927 A | 9/1997 | Boebel et al. |
| 5,672,945 A | 9/1997 | Krause |
| 5,674,179 A | 10/1997 | Bonnet et al. |
| 5,676,497 A | 10/1997 | Kim |
| 5,695,448 A | 12/1997 | Kimura et al. |
| 5,702,420 A | 12/1997 | Sterling et al. |
| 5,709,698 A | 1/1998 | Adams et al. |
| 5,730,752 A | 3/1998 | Alden et al. |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |

(56) References Cited

U.S. PATENT DOCUMENTS

| | | |
|---|---|---|
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,094 A | 7/2000 | Clifford, Jr. et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,171,316 B1 | 1/2001 | Kovac et al. |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,315,714 B1 | 11/2001 | Akiba |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,471,639 B2 | 10/2002 | Rudischhauser et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,663,641 B1 | 12/2003 | Kovac et al. |
| 6,712,773 B1 | 3/2004 | Viola |
| 6,824,544 B2 | 11/2004 | Boebel et al. |
| 6,837,847 B2 | 1/2005 | Ewers et al. |
| 7,025,720 B2 | 4/2006 | Boebel et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,763,033 B2 | 7/2010 | Gruber et al. |
| 7,922,737 B1 | 4/2011 | Cesarini et al. |
| 8,062,214 B2 | 11/2011 | Shener et al. |
| 8,419,626 B2 | 4/2013 | Shener-Irmakoglu et al. |
| 8,574,253 B2 | 11/2013 | Gruber et al. |
| 8,663,264 B2 | 3/2014 | Cesarini et al. |
| 8,678,999 B2 | 3/2014 | Isaacson |
| 8,840,626 B2 | 9/2014 | Adams et al. |
| 8,852,085 B2 | 10/2014 | Shener-Irmakoglu et al. |
| 8,893,722 B2 | 11/2014 | Emanuel |
| 8,932,208 B2 | 1/2015 | Kendale et al. |
| 8,951,274 B2 | 2/2015 | Adams et al. |
| 9,060,800 B1 | 6/2015 | Cesarini et al. |
| 9,060,801 B1 | 6/2015 | Cesarini et al. |
| 9,066,745 B2 | 6/2015 | Cesarini et al. |
| 9,072,431 B2 | 7/2015 | Adams et al. |
| 9,089,358 B2 | 7/2015 | Emanuel |
| 9,125,550 B2 | 9/2015 | Shener-Irmakoglu et al. |
| 9,155,454 B2 | 10/2015 | Sahney et al. |
| 9,782,193 B2* | 10/2017 | Thistle ............... A61B 17/1622 |
| 10,631,889 B2 | 4/2020 | Brown et al. |
| 2001/0039963 A1 | 11/2001 | Spear et al. |
| 2001/0047183 A1 | 11/2001 | Privitera et al. |
| 2002/0058859 A1 | 5/2002 | Brommersma |
| 2002/0165427 A1 | 11/2002 | Yachia et al. |
| 2003/0050603 A1 | 3/2003 | Todd |
| 2003/0050638 A1 | 3/2003 | Yachia et al. |
| 2003/0078609 A1 | 4/2003 | Finlay et al. |
| 2003/0114875 A1 | 6/2003 | Sjostrom |
| 2004/0092992 A1* | 5/2004 | Adams ............. A61B 17/32002 |
| | | 606/180 |
| 2004/0204671 A1 | 10/2004 | Stubbs et al. |
| 2005/0043690 A1 | 2/2005 | Todd |
| 2005/0085692 A1 | 4/2005 | Kiehn et al. |
| 2005/0240206 A1 | 10/2005 | Sjostrom |
| 2006/0036132 A1 | 2/2006 | Renner et al. |
| 2006/0047185 A1 | 3/2006 | Shener |
| 2006/0206134 A1* | 9/2006 | Conquergood ............................. |
| | | A61B 17/320016 |
| | | 606/180 |
| 2006/0241586 A1 | 10/2006 | Wilk |
| 2007/0156161 A1* | 7/2007 | Weadock ............... A61M 1/774 |
| | | 606/170 |
| 2008/0015621 A1 | 1/2008 | Emanuel |
| 2008/0058588 A1 | 3/2008 | Emanuel |
| 2008/0058842 A1 | 3/2008 | Emanuel |
| 2008/0097468 A1 | 4/2008 | Adams et al. |
| 2008/0097469 A1 | 4/2008 | Gruber et al. |
| 2008/0097470 A1 | 4/2008 | Gruber |
| 2008/0097471 A1 | 4/2008 | Adams et al. |
| 2008/0135053 A1 | 6/2008 | Gruber et al. |
| 2008/0146872 A1 | 6/2008 | Gruber et al. |
| 2008/0146873 A1 | 6/2008 | Adams et al. |
| 2008/0245371 A1 | 10/2008 | Gruber |
| 2008/0249366 A1 | 10/2008 | Gruber et al. |
| 2008/0249534 A1 | 10/2008 | Gruber et al. |
| 2008/0249553 A1 | 10/2008 | Gruber et al. |
| 2008/0262308 A1 | 10/2008 | Prestezog et al. |
| 2009/0082628 A1 | 3/2009 | Kucklick et al. |
| 2009/0270812 A1 | 10/2009 | Litscher et al. |
| 2009/0270895 A1 | 10/2009 | Churchill et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0087798 A1 | 4/2010 | Adams et al. |
| 2010/0152647 A1 | 6/2010 | Shener et al. |
| 2010/0152760 A1* | 6/2010 | Mark ............... A61B 17/32002 |
| | | 606/180 |
| 2011/0166419 A1 | 7/2011 | Reif et al. |
| 2012/0078038 A1 | 3/2012 | Sahney et al. |
| 2013/0131452 A1 | 5/2013 | Kuroda et al. |
| 2014/0031834 A1 | 1/2014 | Germain et al. |
| 2015/0018710 A1* | 1/2015 | Furlong ............. A61B 1/00133 |
| | | 600/563 |

OTHER PUBLICATIONS

Written Opinion issued in corresponding International Application No. PCT/US2015/066111 dated Jun. 23, 2016, 9 pages.
International Preliminary Report on Patentability issued in corre-

(56) References Cited

OTHER PUBLICATIONS sponding International Application No. PCT/US2015/066111 dated Jun. 20, 2017, 10 pages.
Australian Examination Report issue in corresponding Australian Application No. 2015364676 dated Sep. 26, 2019, 3 pages.
European Communication Pursuant to Article 94(3) EPC issued in corresponding European Application No. 15 830 921.1 dated Aug. 9, 2021, 7 pages.
Chinese Office Action issued in Chinese Application No. 201580072549.4 dated May 14, 2019, 10 pages.

* cited by examiner

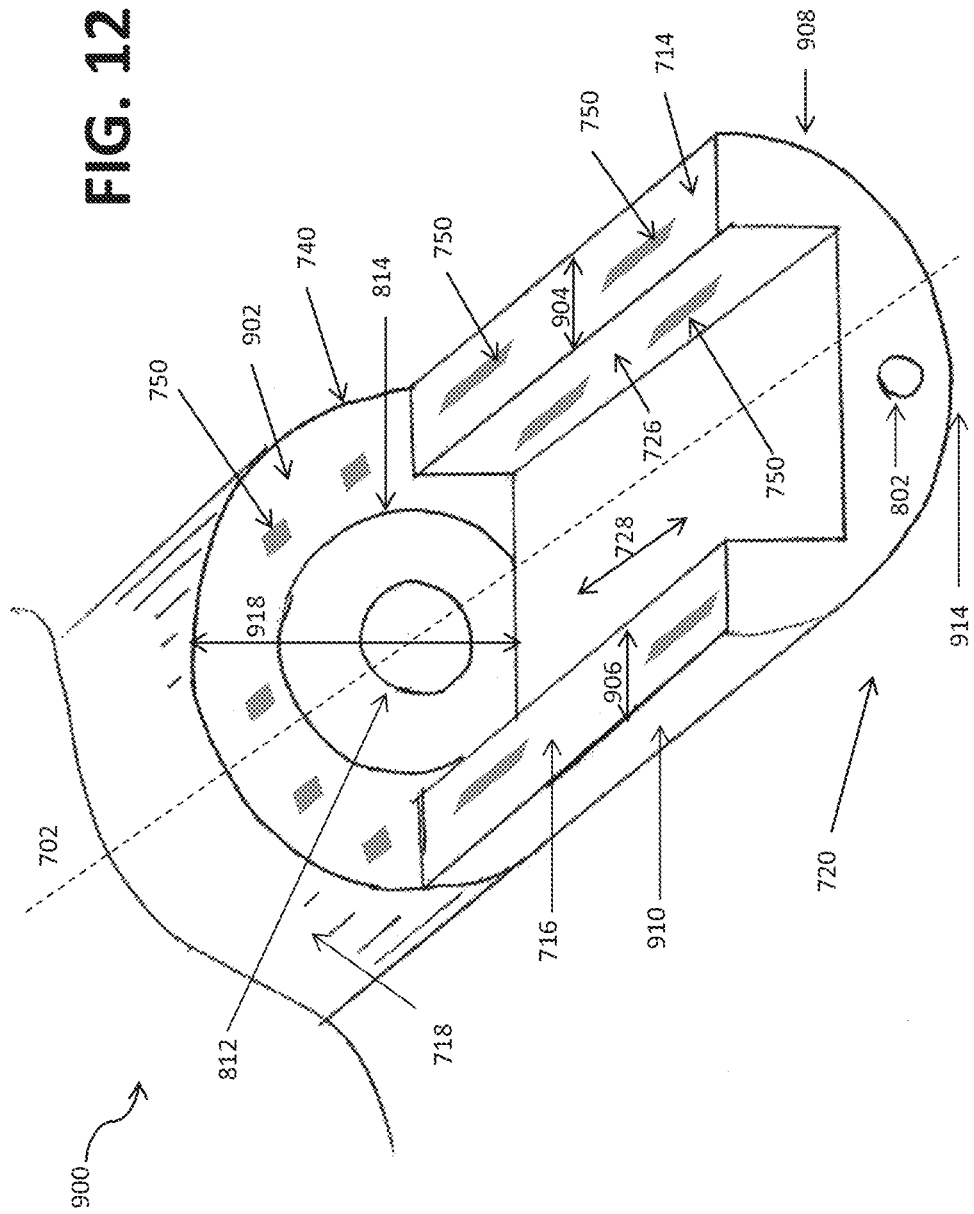

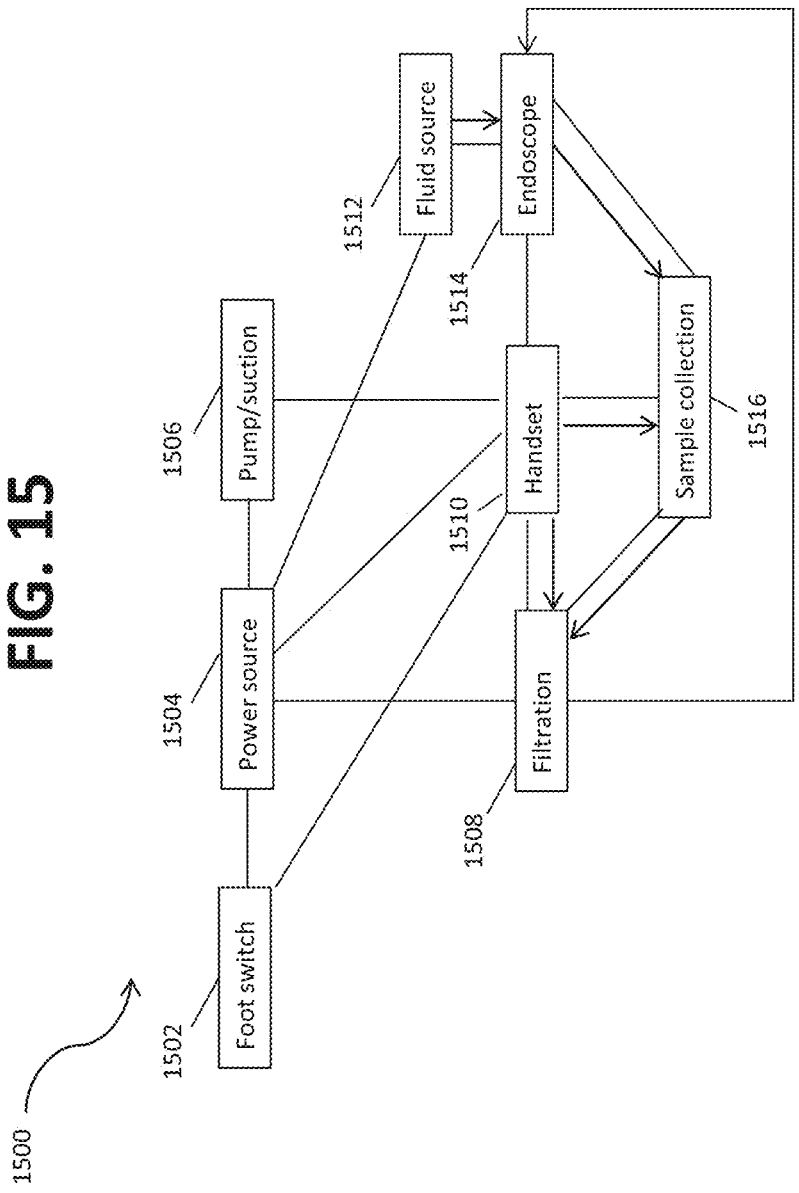

SURGICAL DEVICE WITH INCORPORATED TISSUE EXTRACTION

CROSS-REFERENCE TO RELATED APPLICATIONS

The present application is a continuation of U.S. patent application Ser. No. 15/535,136, filed on Jun. 12, 2017, "Surgical Device with Incorporated Tissue Extraction," which is a U.S. National Stage Application under 35 U.S.C. § 371(a) of PCT/US2015/066111, "Surgical Device with Incorporated Tissue Extraction," filed Dec. 16, 2015, which claims priority to U.S. Provisional Patent App. No. 62/092,698, "Surgical Device Including a Footswitch," filed Dec. 16, 2014, and U.S. Provisional Patent App. No. 62/092,686, "Surgical Device with Incorporated Tissue Extraction," filed Dec. 16, 2014, the entire contents of each of which are hereby incorporated herein by reference.

BACKGROUND

Endoscopic surgery of a distensible organ, such as a uterus, may be performed with an endoscope that is insertable into an organ such as the uterus and a resector that passes through the endoscope to cut or otherwise treat tissue in the organ. During surgery, it often is desirable to distend the organ, such as the uterus, with a fluid, such as saline, sorbitol, or glycine, in order provide a visible working space. Fluid can be infused into the uterus and removed from the uterus through the endoscope and/or the resector.

SUMMARY

According to implementations of the present concepts, tissue resecting systems include easy-to-handle handsets that compactly integrate a pump and other components for extracting fluid/tissue from an organ. In an example implementation, a tissue resecting system includes a handset that includes a disposable portion including a pump, a first fluid line, and a second fluid line. The pump draws fluid, with suction, from an organ through the first fluid line and moves the fluid into the second fluid line for further processing. The handset also includes a reusable portion that is detachably coupled to the disposable portion to define a single housing for the handset. The reusable portion includes one or more drive components that drive the pump. The system also includes a cutting element that extends from the handset to cut tissue from the organ. This cutting element may also be driven by the one or more drive components in the reusable portion. The fluid drawn from the organ by the pump carries tissue that the cutting element cuts from the organ.

In some cases, the disposable portion may include a filtration system that filters the fluid drawn from the organ, where the pump moves the fluid through the filtration system and into the second fluid line, which delivers the filtered fluid back to the organ. The tissue resecting system may include an endoscope that is configured to be inserted into the organ and to guide the cutting element into the organ. The endoscope includes a passageway that is configured to extend into the organ, and the passageway is coupled to the second fluid line to deliver the filtered fluid to the organ. In other cases, the second fluid line may simply deliver the fluid to an external receptacle, for example, for disposal.

In another example implementation, a tissue resecting system includes a handset that includes a disposable housing including a pump, a first fluid line, a second fluid line, and one or more drive components that drive the pump. The pump draws fluid, with suction, from an organ through the first fluid line and moves the fluid into the second fluid line for further processing. The tissue resecting system includes a cutting element that extends from the handset to cut tissue from the organ. The fluid drawn from the organ by the pump carries tissue cut from the organ by the cutting element. The housing may include more than one section. For example, the housing may include a first section and a second section, where the first section includes the pump, the first fluid line, and the second fluid line, and the second section includes the one or more drive components.

The one or more drive components in the reusable portion may include a motor that drives the pump and optionally the cutting element. The motor may be powered by an external power source and/or by a battery in the handset.

According to additional aspects of the present disclosure, implementations structurally integrate various functions of a tissue resecting system into a footswitch. Such integration results in a smaller footprint for the tissue resecting system and makes the system more portable and easier to set up and operate.

In an example implementations, a tissue resecting system includes a resector and a footswitch. The resector includes a handset and a cutting element that extends from the handset to cut tissue from the organ. The footswitch is coupled to the resector and is selectively operated to activate the cutting element. The footswitch includes one or more control elements that control the operation of the cutting element according to selected parameters. The footswitch may include a motor that is coupled to and drives the cutting element via a flexible drive shaft, where the one or more control elements control the motor to drive the cutting element.

The handset may include a pump and a filtration system that recirculates and filters fluid through the organ through fluid lines that pass into the handset. The motor of the footswitch also drives the pump with the flexible drive shaft to move the fluid through the recirculation path. In alternative implementations, the pump and filtration system may be disposed externally from the handset. In some cases, the pump and the filtration system are integrated into the footswitch.

Other aspects a tissue resecting system may be further integrated into the footswitch. For example, the footswitch may include a user interface with a display and user inputs. The user inputs receive the selected parameters employed by the one or more control elements in the footswitch.

In an embodiment, a tissue resecting system, comprising: a disposable portion comprising: a handle portion that defines a hub section and a mating section, the handle defines a fluid path that extends through the hub section and the mating section; an elongated shaft coupled to the hub section of the handle portion, the elongated shaft defines an internal flow channel fluidly coupled to the fluid path, and a central axis; an aperture through a distal end of the elongated shaft; a cutting blade within the elongated shaft and in operational relationship to the aperture; a rotating hub disposed within hub section and in operational relationship to a portion of the fluid path within the hub section, the rotating hub defines a drive connector exposed at a transition between the hub section and the mating section; a blade drive shaft that mechanically couples the cutting blade to the rotating hub, the blade drive shaft disposed within the internal flow channel of the elongated shaft and also disposed in the portion of the fluid path in the hub section; a seal in operational relationship to the rotating hub and the hub section, the seal fluidly isolates the fluid channel from drive connector exposed at the transition between the hub section and the mating section; and a reusable portion comprising: an exterior case detachably coupled to the mating section of the of the disposable portion, the exterior case defines an internal volume; a plurality of drive components disposed at least partially within the internal volume of the reusable portion, and wherein the plurality of drive components are configured to rotate the rotating hub when the tissue resecting device is in use; a power source coupled to the reusable portion.

In an embodiment, a disposable handset component comprising: a handle portion that defines a hub section and a mating section, the handle defines a fluid path that extends through the hub section and the mating section; an elongated shaft coupled to the hub section of the handle portion, the elongated shaft defines an internal flow channel fluidly coupled to the fluid path, and a central axis; an aperture through a distal end of the elongated shaft; a cutting blade within the elongated shaft and in operational relationship to the aperture; a rotating hub disposed within hub section and in operational relationship to a portion of the fluid path within the hub section, the rotating hub defines a drive connector exposed at a transition between the hub section and the mating section; a drive shaft that mechanically couples the cutting blade to the rotating hub, the drive shaft disposed within the internal flow channel of the elongated shaft and also disposed in the portion of the fluid path in the hub section; a seal in operational relationship to the rotating hub and the hub section, the seal fluidly isolates the fluid channel from drive connector exposed at the transition between the hub section and the mating section.

In an embodiment, a method comprising: disposing a cutting element in proximity to an organ, wherein the cutting element is disposed on a distal end of an elongated shaft being part of a handset that comprises a reusable portion and a disposable portion, wherein the handset is coupled to a power source, a footswitch, a filtration system, and a pump; activating the cutting element by applying power from the power source to the handset, wherein the reusable portion comprises a motor that drives the cutting element; removing, from the organ, fluid and tissue by way a fluid path extending through the disposable portion, wherein the motor is fluidly isolated from the fluid path by a seal and the removed fluid and tissue does not contact with the reusable portion, the removing creates removed fluid; recirculating the removed fluid by: transferring the removed fluid and tissue to the filtration system by way of an outflow line coupled to the handset; filtering the tissue from the removed fluid using the filtration system; and returning to the organ at least some of the removed fluid after filtering.

BRIEF DESCRIPTION OF THE DRAWINGS

FIG. 12 is a perspective view of the disposable portion, illustrated from the proximal end looking towards the distal end in order to illustrate the locking and other mating features.

FIG. 15 illustrates a system diagram for a tissue resecting system according to certain embodiments of the present disclosure.

Figure 1:
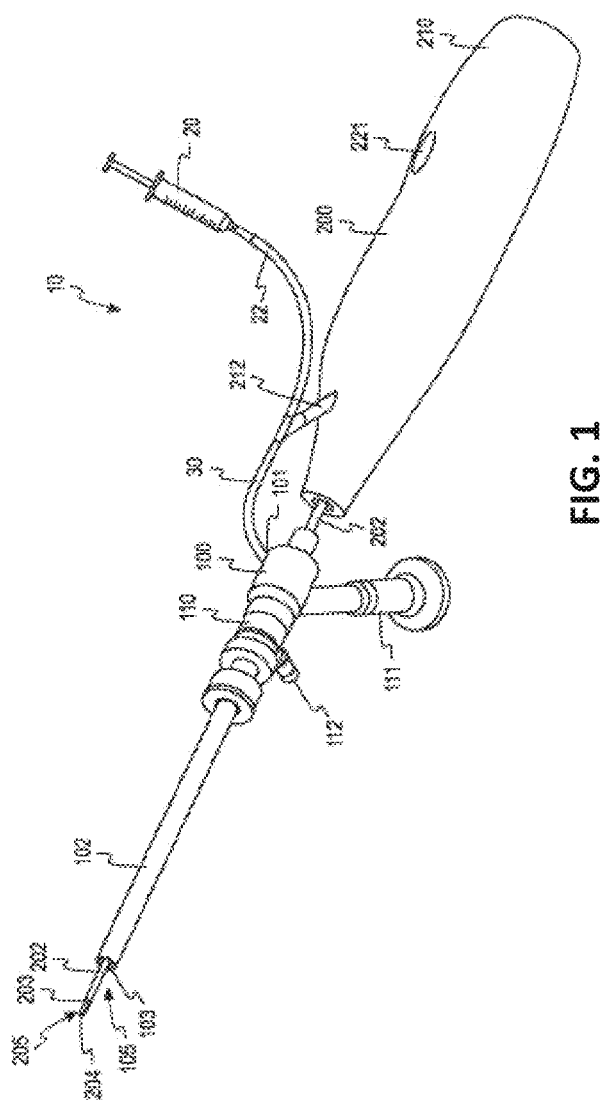
FIG. 1 is a perspective view of a tissue resecting system according to some implementations of the present disclosure.

While the disclosure is susceptible to various modifications and alternative forms, specific implementations thereof have been shown by way of example in the drawings and will be described in detail herein. It should be understood, however, that it is not intended to limit the disclosure to the particular forms disclosed, but on the contrary, the intention is to cover all modifications, equivalents, and alternatives falling within the spirit of the present disclosure.

DEFINITIONS

Certain terms are used throughout the following description and claims to refer to particular system components. As one skilled in the art will appreciate, different companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

"Drive shaft" shall mean a device that transmits energy from a first point (e.g., a rotational hub) to a second point (e.g., a cutting blade). The terms "drive shaft" shall not be read to imply any particular structure unless expressly so limited. Thus, a drive shaft may be implemented as a solid rod, a tube with hollow central axis, an elongated spring, and the like.

"Detachably coupled" shall mean that two components are designed and constructed to be selectively coupled to each other, and also selectively decoupled from each other, without damage to or destroying either component. Thus, if a first device must be broken, destroyed, or rendered fully or partially inoperable as part of decoupling from the second device, then such devices shall not be considered "detachably coupled" within the meaning of this specification and claims.

An "elliptical feature" shall mean a feature that defines a closed curve on a plane surrounding two focal points such that the sum of the distances to the two focal points is constant for every point on the curve. A circular feature is a special case of the elliptical feature where the two focal points are collocated.

DETAILED DESCRIPTION

The following discussion is directed to various embodiments. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Operating rooms (OR) may have limited space due to the number of personnel and the amount of equipment that may be employed for some procedures. As such, the systems, apparatuses, and methods discussed herein are directed towards instrumentation designed to reduce clutter in the OR during procedures and to reduce the cross-contamination potential among and between patients using disposable and reusable components as discussed herein. In an embodiment, a footswitch of a device such as a tissue resecting device comprises components enabling device control, device power, and tissue extraction in a foot unit (foot switch) that may be used as an on/off switch in similar devices. In another embodiment, a handset of the device may comprise a pump (miniature pump), in contrast to other devices that may rely on a pump or other suction source situated in a control unit or otherwise supplied by OR services as a separate unit from the device. In various embodiments, the pump in the handset may be coupled to a filtration system to recirculate the carrying medium to the body and to capture the removed materials, and in other embodiments the pump may be coupled to an open ended extraction pass where the carrying medium is not recovered (recirculated). In some embodiments, the device may not operate on a mechanical cutting principle that employs power, in which case a drive motor may be employed for the pump.

In an embodiment, the footswitch may comprise a printed circuit board (PCB) and a transformer, and the controls for the removal process may be housed in a separate display unit that may be located inside or outside of the sterile field. In another embodiment, the footswitch may include a graphical user display that may be a touch screen and may include control buttons for the display, a motor to drive at least the cutting action may also be included in some embodiments, as may a means of extracting and/or transporting medium. The footswitch may further include a means of separating the products of tissue removal from the carrying medium (fluid), and may be configured to return the separated carrying medium to the body and/or contain the tissue or other removal products for further analysis. The battery in the footswitch may be configured to carry enough power for procedures within a predetermined time period without recharging, which decreases or eliminates the use of a power cord during the procedure.

In an embodiment, a tissue resecting device comprises a handset that comprises a motor but not a pump and is made up of a disposable part and a reusable part which are fluidly isolated from each other so that the reusable portion is not in contact with the fluid path, or in some embodiments, so that only a portion separate and fluidly isolated from the motor, heat sink, and electronics of the reusable portion is in contact with the fluid. In an embodiment, the handset comprises the motor to activate the tissue resecting device, a plurality of electronics including a PCB to control the motor, a flow path to transfer fluid from the tissue removal device to external collection containers, a tissue resecting device (e.g., a cutting blade) that simultaneously resects and removes tissue from a target area. In an embodiment, a vacuum/power unit, which may be referred to generically as a control box or external source, comprises a vacuum generator (pump) employed to move fluid from the organ through the tissue resecting device and the disposable part of the handset and into the external collection device, where the power source used to power the motor in the handset is also located. In an embodiment, the control box may comprise a graphical user interface, which may display various statistics and information regarding the device, the current procedures, and historical procedural information, such as the time that has passed since a procedure began. A footswitch may also be coupled to the device, the footswitch may comprise a single pedal for handset motor activation as well as other components as discussed herein.

In an embodiment, the handset may comprise a reusable portion and a disposable portion. In example systems the reusable portion shares a central axis with the disposable portion, along which they are aligned in order to provide power to a cutting element and establish a fluid path from the target organ to a container for collection and/or disposal. In an embodiment, the reusable portion of the handset may comprise an outer casing comprising a distal end and a proximal end, the distal end configured to engage with a proximal portion of a connector of the disposable portion. The outer casing may also comprise a plurality of mating features including rails that are intended to mate with a guide track of the disposable portion along a shared (common) central axis. In an embodiment, the outer casing of the reusable portion may comprise a plurality of tabs or other features located on the distal end and on a first and a second side, these tabs may be configured to mate with features of the disposable portion. In an embodiment, disposed in the outer casing of the reusable portion are a motor and a heat sink (which may be collectively referred to herein as the motor), as well as a plurality of electronics. The disposable portion may comprise a distal end comprising a housing coupled to a cutting element or other instrument and a proximal end configured to be coupled to a sample collection, filtration, or other fluid and/or tissue receptor or fluid recirculation device. The disposable portion comprises a fluid path that moves fluid and/or tissue from the organ through the handset and on to the sample collection, filtration, or other fluid and/or tissue receptor or fluid recirculation device without contacting the reusable portion.

In an embodiment, the fluid path in the disposable portion is fluidly isolated from the reusable portion and extends from the distal end of the handset through a rotating hub to a proximal end of the disposable portion. In an embodiment, the seal separates the fluid flow from the motor and heat sink and electronics, which may eliminate the need for an autoclaving procedure in between surgical procedures. For example, a disposable portion may be attached to the reusable portion, a procedure performed, the disposable portion may be removed, disposed, and the reusable portion may be cleaned by spraying, wiping, or other means, and the reusable portion is prepared (cleaned) for a subsequent surgery with a new disposable portion without being sterilized (by autoclave or otherwise), since the non-sterile fluid and tissue in the disposable portion do not come in contact with the reusable portion.

In another embodiment, the fluid path comprises a first portion extending from the distal end of the disposable portion to a rotating hub of the reusable portion, where a seal is disposed as discussed above. In this embodiment, the fluid path does not take a 90 degree turn with respect to the central axis, but rather comprises a second portion disposed before the end of the first portion and comprising a smooth angled transition. After the transition, the second portion extends parallel to the central axis towards the proximal end of the disposable portion where the fluid and/or tissue are collected/disposed/recirculated, depending upon the embodiment.

Referring to FIG. 1, a tissue resecting system 10 includes an endoscope 100 (e.g., a hysteroscope), which includes an endoscope body 110 and an insert portion 102 that extends from the endoscope body 110 to a distal end thereof. The endoscope insert portion 102 is insertable into an organ, (e.g., a uterus) of a patient to enable a tissue resecting procedure in the organ. The tissue resecting system 10 also includes a resector 200 that is received by the endoscope 100 to resect tissue from the organ. The resector 200 includes a handset 210 that is disposed at a proximal end of the endoscope body 110. The resector 200 also includes a shaft 202 that extends from the handset 210 and passes correspondingly through the endoscope body 110 and the endoscope insert portion 102. At the distal end of the shaft 202, the shaft 202 includes a cutting element 204, (e.g., a hysteroscopic tissue removal device). The cutting element 204 is disposed beyond the distal end of the endoscope insert portion 102 to access tissue in the organ. The handset 210 includes a motor (not shown) that is coupled to and drives the cutting element 204 to cut tissue from the organ. A motor, discussed below in FIG. 2, may actuate/rotate and/or linearly move the cutting element 204 in a back-and-forth motion to generate a cutting action.

The endoscope 100 includes an inlet port 101 that is coupled to a main inflow line 30, which delivers fluid, (e.g., saline, sorbitol, glycine, etc.) to the endoscope 100. An endoscope inflow passageway 103 is formed in the endoscope 100 and extends from the inlet port 101 to an inflow opening 105 at the distal end of the endoscope insert portion 102. As shown in FIG. 1, the main inflow line 30 receives fluid from a fluid source 20 (e.g., a syringe or other device) that provides the fluid under some pressure, through a source inflow line 22. The fluid then flows from the main inflow line 30, through the inlet port 101, the inflow passageway 103, and the inflow opening 105, and into the organ at the distal end. In some implementations, the endoscope 100 may include a seal (e.g., a cervix seal) disposed about the endoscope insert portion 102 to close the opening to the organ when the endoscope insert portion 102 is inserted into the organ and to minimize the amount of fluid loss from the organ and the closed loop of the tissue resecting system 10.

The resector 200 includes an outflow opening 205 at the cutting element 204. An outflow passageway 203 extends from the outflow opening 205, through the shaft 202, and into the handset 210. The handset 210 applies suction through the outflow passageway 203. As the cutting element 204 cuts tissue from the organ, the suction draws fluid as well as cut tissue and other byproducts (e.g., blood, etc.) from the cutting process through the outflow opening 205. The fluid, tissue, and byproducts then flow through the outflow passageway 203 and into the handset 210. In other implementations, the handset 210 may be coupled to an outflow passageway formed in the endoscope insert portion 102 (rather than the shaft 202) and the suction extracts the fluid, tissue, and other byproducts through this alternative outflow passageway formed in the endoscope insert portion 102.

After receiving the fluid, tissue, and other byproducts from the organ through the outflow passageway 203, the handset 210 filters the fluid to remove the tissue and other byproducts. The handset 210 includes an inflow line 212 that is coupled to the main inflow line 30 to deliver the filtered fluid back to the main inflow line 30. Thus, the main inflow line 30 receives fluid from the handset 210 as well as the fluid source 20. The filtered fluid flows through the inflow passageway 103 of the endoscope 100 and into the organ.

The handset 210 includes a pump that recirculates the fluid through the tissue resecting system 10 and the organ. In addition, the handset 210 includes a filtration system that removes tissue and other byproducts from the recirculating fluid. Furthermore, the handset 210 includes a control switch/button 221 that activates the pump and/or the cutting element 204. In some implementations, the handset 210 may also include a battery. In other embodiments, the pump and/or the cutting element 204 may be activated by an external footswitch coupled to the handset 210.

To summarize the fluid path in the tissue resecting system 10, fluid is introduced into the system through the source inflow line 22 from the fluid source 20. The fluid from the source inflow line 22 flows through the main inflow line 30, the inlet port 101, the inflow passageway 103, and the inflow opening 105 and into the organ. The fluid, tissue, and other byproducts produced by the cutting element 204 are then drawn from the organ through the outflow opening 205, the outflow passageway 203, and into the handset 210. The fluid is filtered in the handset 210 and flows through the inflow line 212 and back into the main inflow line 30. Thus, the handset 210 illustrated in FIG. 1 is configured to extract fluid from an organ and filter the fluid for delivery back into the organ. Recirculating the fluid in this manner minimizes the amount of working fluid required for a procedure. Fluid from the fluid source 20 can also be subsequently introduced to the tissue resecting system 10 to maintain an amount of fluid in the system, for example, in the event of some leakage.

In contrast to other tissue resecting systems that require many separate components to be organized, the handset 210 integrates many of the components required for recirculating fluid through an organ as well as cutting and extracting tissue from the organ. Advantageously, the configuration of the handset 210 makes the tissue resecting system 10 highly portable and easier to set up. Additionally, due to the compact nature of the tissue resecting system 10, less fluid is required to create the necessary flow through the endoscope 100 and the resector 200. As such, the fluid can be more easily managed to maintain fluid pressure inside the organ, for example, for distension. In addition, the amount of fluid can be more easily monitored to ensure undesired/excessive absorption of fluid into the body does not occur.

As shown in FIG. 1, the endoscope 100 may also accommodate other devices for various procedures. For example, the endoscope 100 includes a camera port 111 and a light port 112 that may be coupled to a camera (not shown) and an illumination source (not shown), respectively. Together, the camera and the illumination source allow the operator to visualize and capture images from the area around the distal end of the tissue resecting system 10. It is understood, however, that the endoscope 100 is shown as an example, and that other similar devices (with fewer or more features) can be employed according to aspects of the present disclosure, for example, to accommodate the resector 200.

Figure 2:
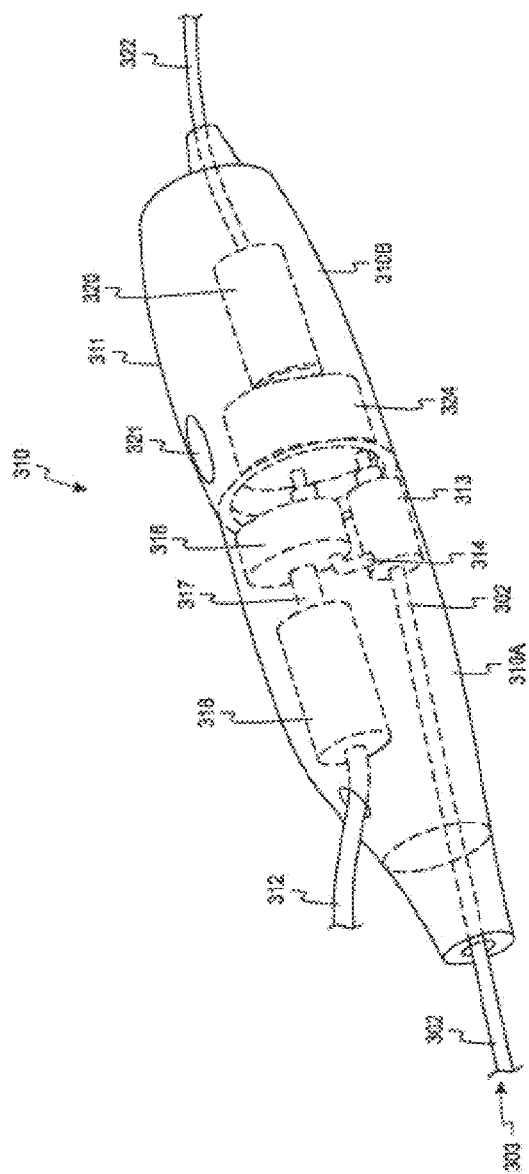
FIG. 2 is a perspective view of a handset for a tissue resecting system according to some implementations of the present disclosure.

Referring to FIG. 2, an example handset 310 is illustrated. The handset 310, for instance, may be employed in the tissue resecting system 10 (e.g., in some implementations the handset 210 is the handset 310 shown in FIG. 2). The handset 310 includes a housing 311 that contains many of the components required for cutting and extracting tissue from an organ and recirculating fluid through the organ. The housing 311 is defined by a disposable portion 310A and a reusable portion 310B. The disposable portion 310A and the reusable portion 310B may be detachably coupled to each other by threaded engagement, snap-fit, frictional engagement, pins, fasteners, tape (adhesive), etc. The disposable portion 310A is intended to be discarded after only one use. Meanwhile, the reusable portion 310B includes components that can be used more than one time. After each use, the disposable portion 310A is detached from the reusable portion 310B and discarded, but the same reusable portion 310B can be coupled to a new disposable portion similar to 310A for another use. Each disposable portion 310A may be individually and sterilely packaged. Allowing the section 310A to be disposable promotes hygienic use of the tissue resecting system 10 (e.g., including the handset 310), because it eliminates any need to clean and sterilize the disposable portion 310A after it has been contaminated, for example, by contact with fluid and tissue from a patient. In addition, allowing the reusable portion 310B to be reused reduces cost, because it does not require all components of the tissue resecting system 10 to be discarded after only one use. Advantageously, the tissue resecting system 10 provides the convenience of disposable components while avoiding the costs of a completely disposable handset, thus increasing efficiency and safety in the OR without increasing cost.

The handset 310 includes a shaft 302 that has a cutting element at a distal end. Similar to the implementation shown in FIG. 1, the handset 310 in FIG. 2 receives fluid from the organ and then returns filtered fluid to the organ through an inflow line 312. As shown in FIG. 2, the shaft 302 extends from the housing 311 of the handset 310. Like the shaft 202 described above, the shaft 302 provides an outflow passageway 303 that delivers the fluid, tissue, and other byproducts into the handset 310. The shaft 302 is coupled to a chamber 313 where the fluid, tissue, and other byproducts are drawn from the outflow passageway 303.

The handset 310 includes a pump 316 inside the housing 311. The pump 316 is coupled to the chamber 313 via an outflow line 314. The pump 316 is capable of producing sufficient suction at the distal end of the resector to draw the fluid from the organ and through the outflow passageway 303, the chamber 313, and the outflow line 314. The pump is sufficiently compact to permit the handset 310 to have a convenient size and an ergonomic shape for easy handling. The pump 316 may be a positive displacement pump, such as a gear pump, a diaphragm pump, a peristaltic pump, a cavity pump, a lobe pump, a piston pump, or the like. The magnitude of suction depends on the cutting device, the nature of tissue being cut, and the hydraulic resistance in the extraction path. The suction, for example, may be produced with a vacuum of approximately 100 mmHg to approximately 500 mmHg. It is understood, however, that the vacuum may be provided according to a range, for example, with a maximum greater than 500 mmHg, as required by the operation of the tissue resecting system.

The handset 310 also includes a filtration system 318. The pump 316 is coupled to the filtration system 318 via a connecting line 317. Accordingly, the fluid from the outflow line 314 is drawn through the pump 316 and to the filtration system 318 via the connecting line 317. The filtration system 318 includes a filter/tissue trap that removes the tissue and other byproducts from the fluid received by the handset 310. The filter/tissue trap may be removable or otherwise accessible to allow the tissue from the organ to be collected and examined. The filtration system 318 is coupled to the inflow line 312 which allows filtered fluid to be returned to the organ via an endoscope (e.g., endoscope 100) as described above. Although the pump 316 shown in FIG. 2 is upstream of the filtration system 318, it is understood that in other implementations, the components inside the housing 311 may be configured differently so that the pump 316 is downstream of the filtration system 318 and pulls, rather than pushes, the fluid through the filtration system 318.

As shown in FIG. 2, the outflow line 314, the pump 316, the connecting line 317, the filtration system 318, and the inflow line 312 are contained in the disposable portion 310A. These components are contaminated by contact with fluid and tissue from the body. As such, the ability to dispose of them after a single use enhances the convenience of using the handset 310. Because the shaft 302 (with the outflow passageway 303 and the cutting element) also comes into direct contact with the fluid and tissue from the body, it is also conveniently disposable with the other components in the disposable portion 310A.

Additionally, the handset 310 includes a motor 320 to drive the pump 316. In this implementation, the motor 320 is electrically coupled to an external power source, for example, a DC power, via a cable 322. Typically, the tissue extraction and fluid recirculation by the pump 316 and the cutting operation occur at the same time, so the same motor 320 can be used for the pump 316 and the cutting element. Thus, the motor 320 drives the shaft 302 to generate cutting action with the cutting element (e.g., rotating and/or linearly moving the cutting element in a back-and-forth motion to generate the cutting action). Even if a common motor is employed, however, the fluid flow from the pump can be controlled independently from the cutting operation with the cutting element. The handset 310 can include a gear box and clutch 324 that divides the drive from the motor 320 between the pump 316 and the shaft 302.

The handset 310 includes a control switch/button 321 that activates the pump 316 and/or the shaft 302 (and the attached cutting element). In some implementations, the motor 320 runs and drives the pump 316 constantly whenever the cable 322 is coupled to the external power source. Meanwhile, the control switch/button 321 is selectively operated by the user to engage a clutch that delivers drive from the motor 320 to the shaft 302. For example, in some such implementations, the handset 310 constantly recirculates fluid through the organ, while the user selectively presses the control switch/button 321 to cut tissue from the organ. In other implementations, one control switch/button may be employed to activate fluid recirculation with the pump 316, while another control switch/button may be employed to independently and selectively activate the cutting element. In further implementations, the user presses the control switch/button 321 to activate the pump 316 and the cutting element simultaneously. In some embodiments, other controls and user interfaces may be provided to control other aspects of the tissue resecting system 10.

Because the motor 320 and the gear box and clutch 324 are not contaminated by contact with fluid and tissue drawn from the organ, these components can be reused more easily. As such, the motor 320 and the gear box and clutch 324 are positioned in the reusable portion 310B. In some cases, these components may be more costly than those in the disposable portion 310A. As such, reusing the motor 320 and the gear box and clutch 324 reduces the marginal cost of using the tissue resecting system 10. The reusable portion 310B may be cleaned and/or sterilized before it is used again.

Figure 3:
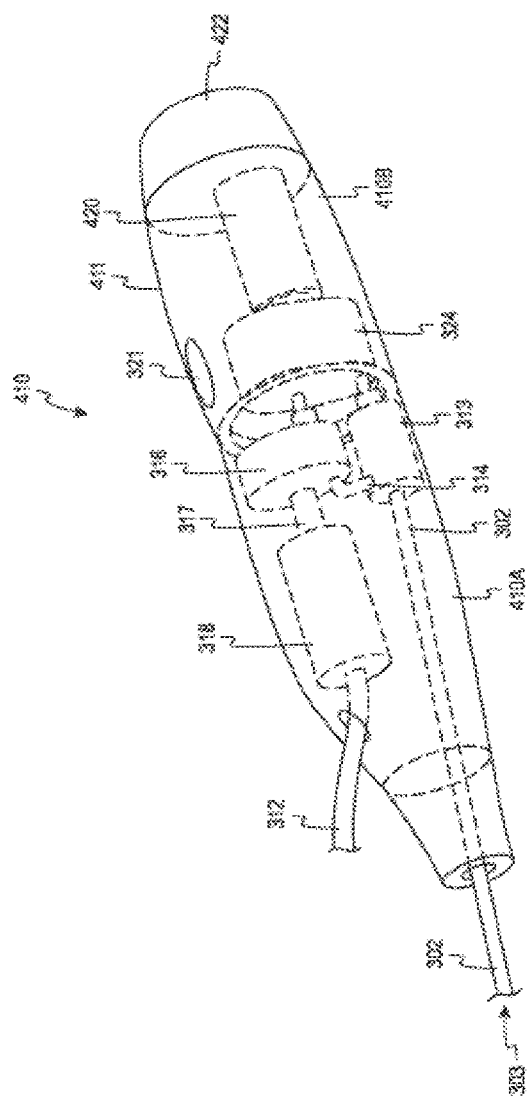
FIG. 3 is a perspective view of another handset for a tissue resecting system according to some implementations of the present disclosure.

Referring to FIG. 3, another example handset 410 is illustrated having a disposable portion 410A and a reusable portion 410B. The handset 410 is similar to the handset 310 described above and includes many of the same components, where like reference numerals indicate like elements across the Figures. Indeed, like the handset 310 in FIG. 2, the handset 410 may be employed in the tissue resecting system 10. The handset 410, however, does not receive power from an external power source. As shown in FIG. 3, the handset 410 does not include a cable that extends outwardly to an external power source. Rather, the handset 410 includes a battery 422 that is coupled to and powers a motor 420, which in turn drives the pump 316 and the shaft 302 via the gear box and clutch 324, as described above. In an embodiment, the battery 422 may be a non-rechargeable battery that must be replaced once its power has been depleted. In other embodiments, the battery 422 may be a rechargeable battery that can be coupled to another power source to be replenished.

As shown in FIG. 3, the battery 422 is conveniently and removably attached to the proximal end of the reusable portion 410B of the handset 410. As such, the handset 410 has a housing 411 that is defined by a differently configured reusable portion 410B. In some aspects, the handset 410 is easier to use as compared with the handset 310 because the motion of the handset 410 is not restricted by a cable that is connected to an external power source.

Figure 4:
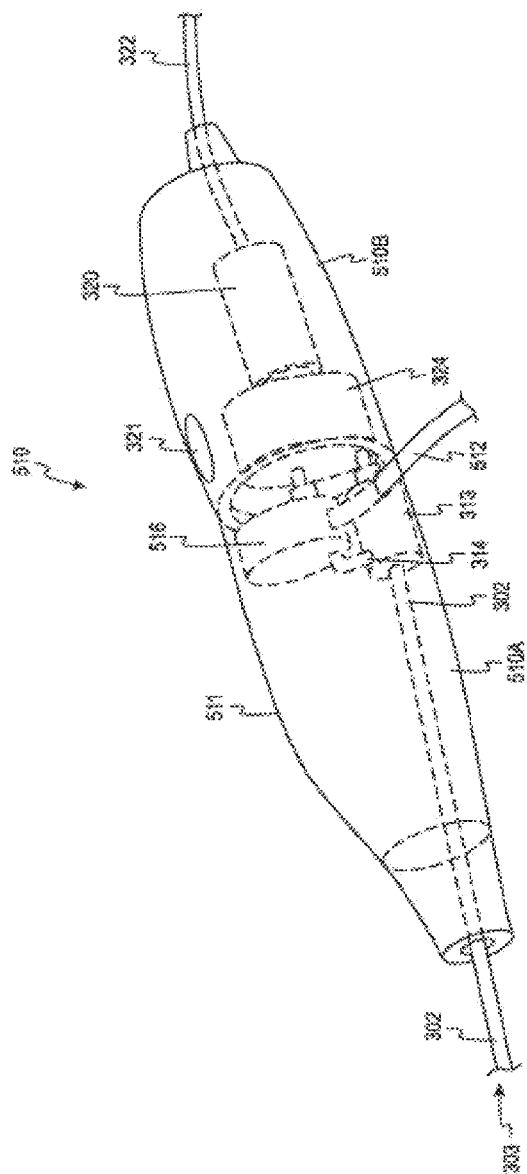
FIG. 4 is a perspective view of yet another handset for a tissue resecting system according to some implementations of the present disclosure.

Referring to FIG. 4, another example handset 510 is illustrated having a disposable portion 510A and a reusable portion 510B. The handset 510 includes many of the same components of the handsets 310 and 410, where like reference numerals indicate like elements across the Figures. Unlike the handsets 310 and 410, however, the handset 510 does not filter and/or recycle the fluid received from the organ.

As shown in FIG. 4, the handset 510 includes a pump 516 that draws fluid/tissue from the organ through the outflow line 314, but the pump 516 does not direct the fluid/tissue to a filtration system and back to the organ. Rather, the fluid/tissue is directed from the handset 510 through an external line 512 to an external receptacle where the fluid/tissue can be collected for disposal, examination, etc. Thus, the handset 510 provides open-ended extraction. With the external line 512, the handset 510 includes a housing 511 that is defined in part by the disposable portion 510A, which has a different configuration as compared with the handsets 310, 410.

According to aspects of the present disclosure, the implementations provide examples of tissue resecting systems that include easy-to-handle handsets that compactly integrate a pump and other components for extracting fluid/tissue from an organ. In some implementations, the handsets include a filtration system to allow fluid to be recirculated through the organ. The handsets include a disposable portion that allows components that contact the fluid/tissue (e.g., the pump) to be easily disposed, thereby promoting hygienic use of the tissue resecting system. Meanwhile, the handsets include a reusable portion that allows other components (e.g., drive components) to be used more than once, thereby achieving cost savings.

Although the implementations described above may include a first section that is disposable and a second section that is reusable, it is understood that the second section in alternative implementations may also be disposable. Thus, the handset may include a housing that is defined by more than one disposable portion.

Figure 5:
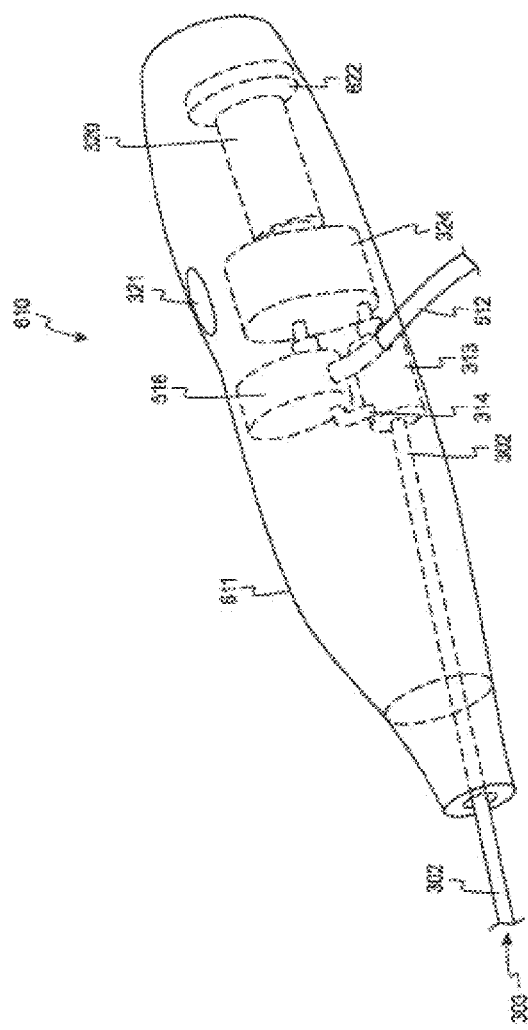
FIG. 5 is a perspective view of a further handset for a tissue resecting system according to some implementations of the present disclosure.

It is also understood that other implementations may employ a single disposable housing. Referring to FIG. 5, for example, another example handset 610 is illustrated. The handset 610 includes a housing 611 that houses the chamber 313, the outflow passageway 314, the pump 516, the gear box and clutch 324, the motor 320, and a battery 622. Like the handset 510 described above, the handset 610 does not filter and recirculate fluid drawn from the organ. In other words, the handset 610 provides open-ended extraction. Driven by the motor 320 via the gear box and clutch 324, the pump 516 draws the fluid, tissue, and other byproducts from the organ into the handset 610 through the outflow passageway 303 and out of the handset 610 through the external line 512. Unlike the handset 510, however, the housing 611 of the handset 610 is not divided into a disposable portion and a reusable portion. Rather, the handset 610 is configured to be completely disposable. The motor 320 and the battery 622 are disposable with the other components of the handset 610. For example, handset 610 may include a low-cost motor and a low-cost battery that make single or limited use of the handset 610 less prohibitive. Therefore, the handset 610 is configured for limited, for example, single, use and convenient disposal. Advantageously, the handset 610 promotes hygienic use of the tissue resecting system 10, because it eliminates any need to clean and sterilize any of its components after it has been contaminated, for example, by contact with fluid and tissue from the patient.

It is understood that aspects of the present disclosure are not limited to the implementations described above. For example, in alternative implementations where the cutting element does not require power or the drive of a motor, the motor in the handset only drives the pump. In other implementations, separate motors may be employed to drive the pump and the cutting element, respectively. In yet other implementations, the motor may be disposed externally and coupled to the handset via a rigid or flexible drive shaft, where the handset includes drive components (e.g., gear box and clutch) that deliver the driving force from the motor to the pump, etc.

It is also contemplated that additional implementations according to aspects of the present disclosure may combine any number of features from any of the implementations described herein. For example, referring to FIGS. 2 and 3, an operator may have the option of selectively coupling the same disposable portion 310A with either the reusable portion 310B (external power source) or the reusable portion 410B (onboard battery power). Or referring to FIGS. 2 and 4, an operator may have the option of selectively coupling the same reusable portion 310B with either the disposable portion 310A (fluid filtration/recirculation) or the disposable portion 510A (open-ended extraction, no fluid filtration/recirculation).

Although the implementations described herein may include an endoscope through which a resector passes, it is contemplated that, in other applications, resectors according to aspects of the present disclosure do not pass through a working channel of an endoscope and instead may be employed outside an endoscope (e.g., work along with the endoscope).

Figure 6:
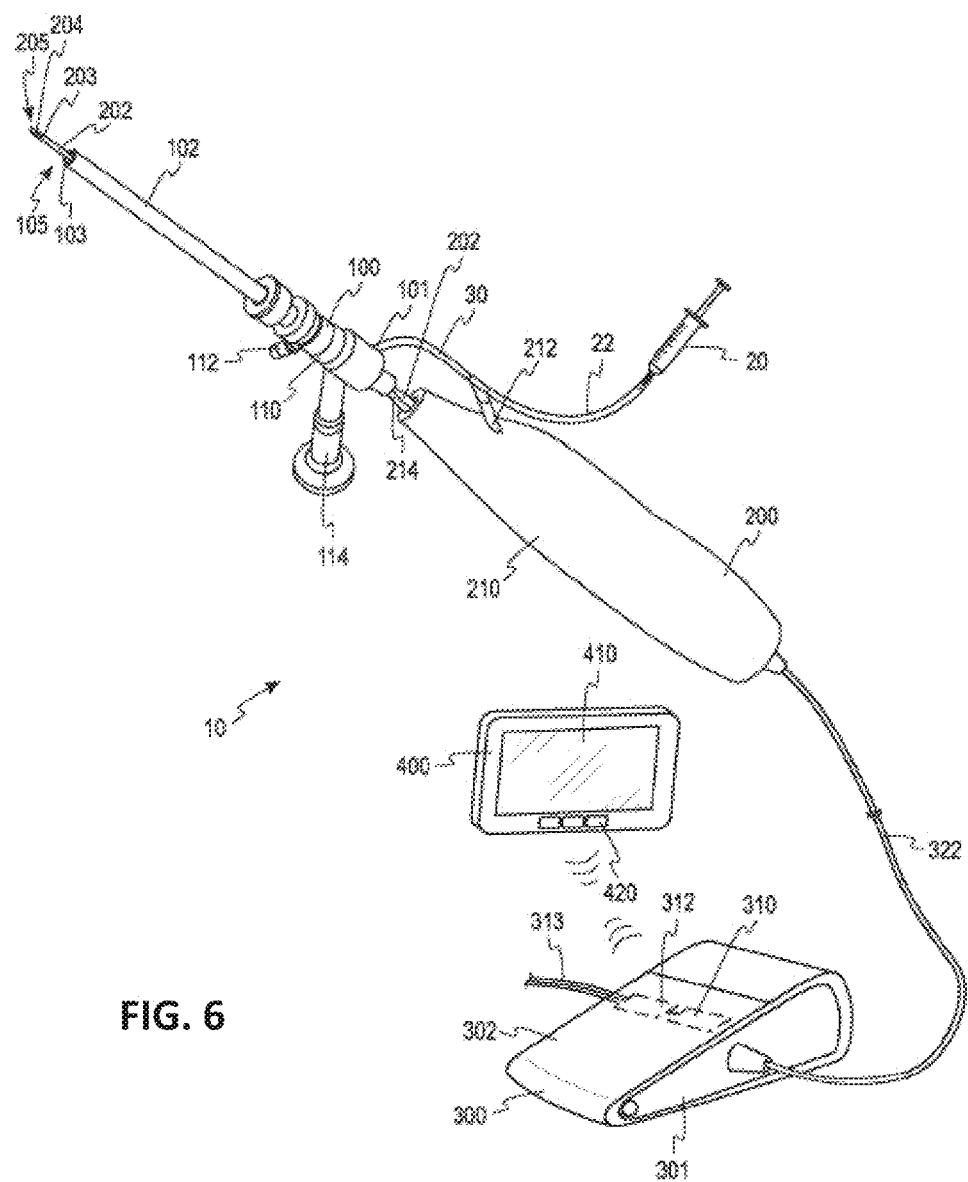
FIG. 6 is a perspective view of a tissue resecting system according to some implementations of the present disclosure.

Referring to FIG. 6, a tissue resecting system 10 includes an endoscope 100 (e.g., a hysteroscope), which includes an endoscope body 110 and an insert portion 102 that extends from the endoscope body 110 to a distal end. The endoscope insert portion 102 is insertable into an organ (e.g., a uterus, a prostate, etc.) of a patient to enable a tissue resecting procedure in the organ. The tissue resecting system 10 also includes a resector 200 that is received by the endoscope 100 to resect tissue from the organ. The resector 200 includes a handset 210 that is disposed at a proximal end of the endoscope body 110. The resector 200 also includes a cutting shaft 202 that extends from the handset 210 and passes correspondingly through the endoscope body 110 and the endoscope insert portion 102. At its distal end, the cutting shaft 202 includes a cutting element 204 that performs tissue resection. The cutting element 204 is disposed beyond the distal end of the endoscope insert portion 102 to access tissue in the organ. The handset 210 transmits a driving force to the cutting element 204 to cut tissue from the organ. The cutting shaft 202 may cause the cutting element 204 to translate, reciprocate, actuate, rotate, or any combination thereof, thereby generating a cutting action.

As shown in FIG. 6, the endoscope 100 may also accommodate other devices for the procedure. For example, the endoscope 100 includes a camera port 114 and a light port 112 that may be coupled to a camera (not shown) and an illumination source (not shown), respectively. Together, the camera and the illumination source allow the operator to visualize and capture images from the area around the distal end of the tissue resecting system 10. It is understood, however, that the endoscope 100 is shown as an example, and that other similar devices (with fewer or more features) can be employed according to aspects of the present disclosure (e.g., to accommodate the resector 200).

The endoscope 100 includes an inlet port 101 that is coupled to a main inflow line 30, which delivers fluid (e.g., saline, sorbitol, glycine, etc.) to the endoscope 100. An endoscope inflow passageway 103 is formed in the endoscope 100 and extends from the inlet port 101 to an inflow opening 105 at the distal end of the endoscope insert portion 102. As shown in FIG. 6, the main inflow line 30 receives fluid from a fluid source 20 (e.g., a syringe) through a source inflow line 22. The fluid then flows from the main inflow line 30, through the inlet port 101, the inflow passageway 103, and the inflow opening 105, and into the organ at the distal end of the endoscope 100.

The resector 200 includes an outflow opening 205 at the cutting element 204. An outflow passageway 203 extends from the outflow opening 205 and through the cutting shaft 202. The handset 210 includes an outflow line 214 that is coupled to a proximal portion of the outflow passageway 203. The handset 210 delivers suction through the outflow line 214 and the outflow passageway 203. As the cutting element 204 cuts tissue from the organ, the suction draws loose tissue as well as fluid from the organ through the outflow opening 205 at the cutting element 204. The fluid/tissue then flows through the outflow passageway 203 and the outflow line 214 into the handset 210. In other implementations, the outflow line 214 of the handset 210 may be coupled to an outflow passageway formed in the endoscope insert portion 102 (rather than the cutting shaft 202) and the suction extracts the fluid/tissue and through the alternative outflow passageway formed in the endoscope insert portion 102.

The tissue resecting system 10 includes a pump that recirculates the fluid through the tissue resecting system 10 and the organ. In addition, the tissue resecting system 10 includes a filtration system that removes tissue and other material from the recirculating fluid. After receiving the fluid/tissue from the organ through the outflow line 214, the tissue resecting system 10 filters the tissue from the fluid. The handset 210 includes an inflow line 212 that is coupled to the main inflow line 30 to deliver the filtered fluid back to the main inflow line 30. Thus, the main inflow line 30 receives fluid from the handset 210 as well as the fluid source 20. The filtered fluid flows through the inflow passageway 103 of the endoscope 100 and into the organ.

To summarize the fluid path in the tissue resecting system 10, fluid is introduced into the tissue resecting system 10 through the source inflow line 22. The fluid from the source inflow line 22 flows through the main inflow line 30, the inlet port 101, the inflow passageway 103, and the inflow opening 105 and into the organ. The fluid and tissue is then drawn from the organ through the outflow opening 205, the outflow passageway 203, the outflow line 214, and into the handset 210. The fluid is filtered and flows through the inflow line 212 and back into the main inflow line 30. Thus, the tissue resecting system 10 illustrated in FIG. 6 is configured to extract fluid from an organ and filter the fluid for delivery back into the organ. Recirculating the fluid in this manner minimizes the amount of working fluid required for a procedure.

As shown in FIG. 6, the tissue resecting system 10 includes a footswitch 300 that activates and controls aspects of the tissue resecting system 10. For example, the footswitch 300 is coupled to the handset 210, via a flexible drive shaft 322, to drive the pump and/or the cutting element 204 (e.g., via the cutting shaft 202). The footswitch 300 may be positioned relative to the endoscope 100 and resector 200 so that the user can manipulate the endoscope 100 and the resector 200 with his/her hands while operating the footswitch 300 with his/her feet. For example, the footswitch 300 may be placed on the floor while the endoscope 100 and the resector 200 are used on a patient disposed above on an operating/examination table. The footswitch 300 includes a body 301 with an upper surface 302. To operate the footswitch 300, the user applies a force against the upper surface 302 (e.g., with his/her foot). For example, the force may cause the upper surface 302 to pivot or to move or otherwise deform mechanically relative to the rest of the body 301, and the mechanical action generates an electrical signal that activates and controls aspects of the tissue resecting system 10. The mechanical action may close an electrical circuit that in turn sends the electrical signal. Or the mechanical action may be otherwise converted into the electrical signal by an appropriate transducer.

The footswitch 300 is configured to minimize the footprint of the tissue resecting system 10. Rather than employing a separate controller device (e.g., computer) to control the pump (e.g., pump 1320 in FIG. 7) and/or the cutting element 204, the tissue resecting system 10 houses control elements 310 in the footswitch 300. The control elements 310 may include one or more printed circuit board (PCB) assemblies with one or more processors that control aspects of the tissue resecting system 10 according to stored program instructions and input parameters. When the footswitch 300 is activated, for example, by the application of a force on the upper surface 302, the resulting electrical signal is delivered to the control elements 310 in the footswitch 300, which in turn activate aspects of the tissue resecting system 10 according to desired parameters. In some implementations, the control elements 310 may cause the cutting element 204 to operate according to a selected cutting speed and/or may cause the pump to recirculate the fluid in the tissue resecting system 10 according to a selected flow rate.

The footswitch 300, as shown in FIG. 6, also contains a suitably rated electrical transformer 312 to convert the main electrical supply into suitable voltages for powering and controlling aspects of the tissue resecting system 10. The footswitch 300 may receive electrical power from an external source via an electrical cable 313. However, the footswitch 300 (and the other implementations described herein) may house a battery of sufficient capacity (e.g., a rechargeable battery) to remove the need for an electrical connection to an external source.

As shown further in FIG. 6, the tissue resecting system 10 includes a separate user interface 400 that allows the user to monitor the operation of the tissue resecting system 10 and to enter any information required for the tissue resecting process. The user may employ the user interface 400 to set parameters for the control elements 310 housed in the footswitch 300. The user interface 400 includes a display screen 410 as well as user inputs 420 (e.g., pushbuttons, switches, etc.). Alternatively or additionally, the user interface 400 may include a touch screen. For example, the user may set a cutting speed for the cutting element 204 and/or set a flow rate for the recirculation of fluid through the tissue resecting system 10. The parameter settings and other input information are communicated to the footswitch 300 for use by the control elements 310. The selected parameters are displayed on the user interface 400 along with any feedback information from the control elements 310.

As shown in FIG. 6, the communication between the footswitch 300 and the user interface 400 occurs over a wireless connection (e.g., via radio frequency (RF) technology, such as BLUETOOTH®, etc.). Using a wireless connection, the user interface 400 can be easily positioned in a desired location, for example, within reach of the surgeon in the sterile field or within reach of an assistant outside the sterile field, without needing to arrange inconvenient cables or wires. However, in alternative implementations, the footswitch 300 and the user interface 400 may communicate over a wired connection.

In contrast to other tissue resecting systems that require many separate components to be assembled and organized, features of the resecting system 10 are compactly integrated into relatively fewer components. As described above, for example, the implementation of FIG. 6 incorporates the control elements 310 into the footswitch 300, thereby eliminating the need for a separate controller device. Reducing the number of separate components in the system saves significant space in the operating room or office environment and minimizes or eliminates the number of trailing hazards posed by tubes and cables. In general, according to aspects of the present disclosure, a footswitch can integrate many of the components required for recirculating fluid through an organ as well as cutting and extracting tissue from the organ. Advantageously, the configuration of the footswitch makes the tissue resecting system 10 highly compact, portable, and easy to set up and operate.

Figure 7:
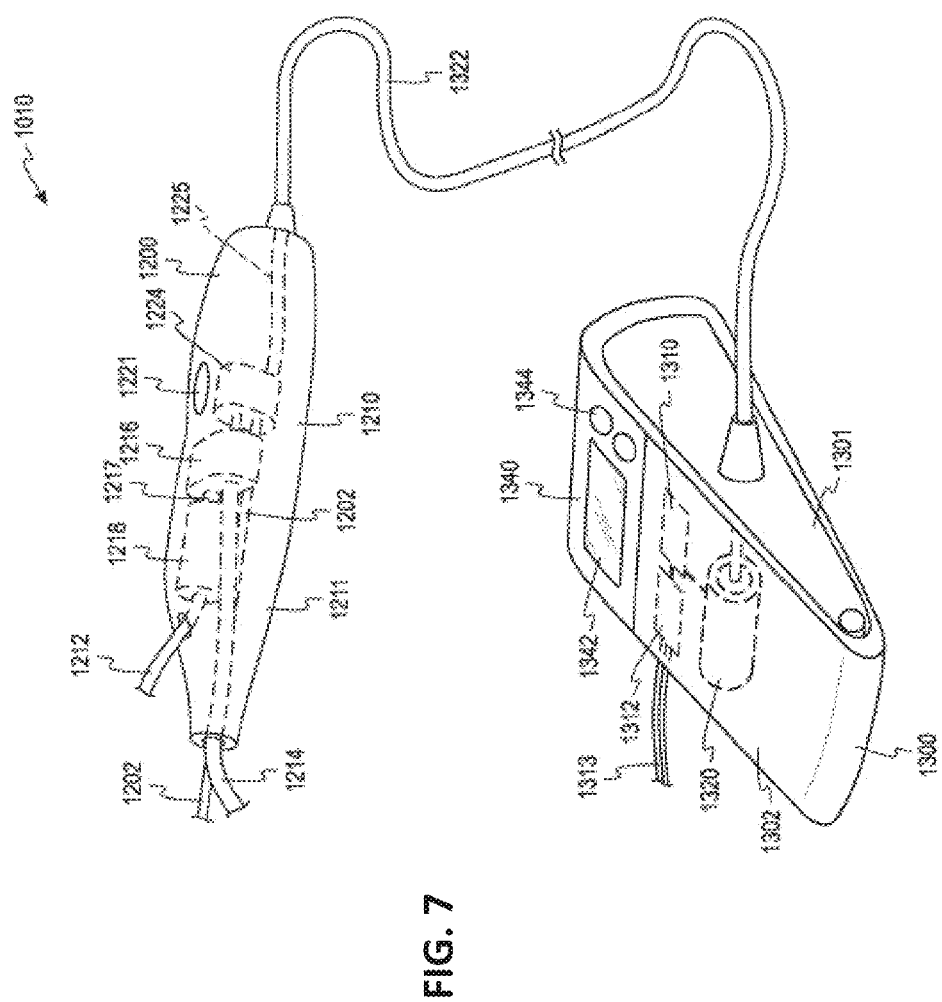
FIG. 7 is a perspective view of another a tissue resecting system according to some implementations of the present disclosure.

Referring to FIG. 7, another implementation of a tissue resecting system 1010 is illustrated. The tissue resecting system 1010 includes a resector 1200, which may be combined with an endoscope (not shown) that is the same as, or similar to, the endoscope 100 of FIG. 6. The resector 1200 includes a handset 1210 with a housing 1211 that contains many of the components required for cutting and extracting tissue from an organ and recirculating fluid through the organ. The resector 1200 also includes a cutting shaft 1202 that extends distally from the handset 1210 and through the endoscope. The cutting shaft 1202 is employed to generate a cutting action (e.g., translating, rotating, reciprocating, or any combination thereof) with a distal cutting element (not shown), which is positioned within an organ by the endoscope.

Similar to the embodiment shown in FIG. 6, the handset 1210 includes an outflow line 1214 that receives fluid from the organ and an inflow line 1212 that returns filtered fluid to the organ. As shown in FIG. 7, the handset 1210 includes a pump 1216 inside the housing 1211. The pump 1216 is coupled to the outflow line 1214 which extends into the housing 1211. The pump 1216 is capable of producing sufficient suction at the distal end of the resector to draw the fluid from the organ and through the outflow line 1214. The pump 1216 is sufficiently compact to permit the handset 1210 to have a convenient size and an ergonomic shape for easy handling. The pump 1216 may be a positive displacement pump, such as a gear pump, a diaphragm pump, a peristaltic pump, a cavity pump, a lobe pump, a piston pump, or the like. The magnitude of suction depends on the cutting device, tissue nature, and the hydraulic resistance in the extraction path. The suction, for example, may be produced with a vacuum of approximately 100 mmHg to approximately 500 mmHg.

The handset 1210 also includes a filtration system 1218. The pump 1216 is coupled to the filtration system 1218 via a connecting line 1217. Accordingly, the fluid from the outflow line 1214 is drawn through the pump 1216 and to the filtration system 1218 via the connecting line 1217. The filtration system 1218 includes a filter/tissue trap that removes the tissue and other material from the fluid received by the handset 1210. The filter/tissue trap may be removable or otherwise accessible to allow the tissue from the organ to be collected and examined. The filtration system 1218 is coupled to the inflow line 1212, which allows filtered fluid to be returned to the organ via an endoscope as described herein. While the filtration system 1218 is shown as being downstream from the pump 1216, in alternative implementations, the filtration system 1218 can be positioned upstream of the pump 1216, such that the fluid is filtered prior to reaching the pump 1216.

Additionally, the tissue resecting system 1010 includes a footswitch 1300. The footswitch includes a motor 1320 to drive the pump 1216. Typically, the tissue extraction and fluid recirculation by the pump 1216 and the cutting operation occur at the same time, so the same motor 1320 can be used for the pump 1216 and the cutting element. Thus, the motor 1320 drives the cutting shaft 1202 to generate the cutting action with the cutting element. Even if a common motor is employed, however, the fluid flow from the pump 1216 can be controlled independently from the cutting operation with the cutting shaft 1202. Thus, the handset 1210 includes a gear box and clutch 1224 that divides the drive from the motor 1320 between the pump 1216 and the cutting shaft 1202. The motor 1320 is coupled to a proximal end of the handset 1210 and drives the gear box and clutch 1224 via a flexible drive shaft 1322. The flexible drive shaft 1322 is coupled to the gear box and clutch 1224 via a connecting drive shaft 1225. The flexibility of the drive shaft 1322 provides sufficient freedom of motion to permit the resector 1200 to be freely manipulated.

The footswitch 1300 includes a body 1301 with an upper surface 1302. Similar to the footswitch 300 of FIG. 6, the user applies a force against the upper surface 1302 (e.g., with his/her foot) to operate the footswitch 1300. Mechanical action resulting from the force against the upper surface 1302 generates an electrical signal that delivers power to and drives the motor 1320, which in turn drives the flexible drive shaft 1322. In some implementations, the user must apply continuous pressure to the upper surface 1302 to drive the motor 1320 continuously. In other implementations, the user applies a force to turn on the power that continuously drives the motor 1320, and the user subsequently applies a separate force to turn off the power to and stop the motor 1320.

The footswitch 1300 also includes control elements 1310 (e.g., PCB assemblies with one or more processors). In particular, the control elements 1310 allow the motor 1320 and thus the flexible drive shaft 1322 to be driven according to selected parameters, such as revolutions per minute (RPM), which in turn determine how the pump 1216 and the cutting element operate.

The handset 1210 includes a control switch/button 1221 that activates the pump and/or the cutting shaft 1202 while the flexible drive shaft 1322 is being driven by the motor 1320. The control switch/button 1221 is selectively operated by the user to engage the gear box and clutch 1224 to deliver drive from the flexible drive shaft 1322 to the cutting shaft 1202 and to the pump 1216. In other implementations, one control switch/button may be employed to activate fluid recirculation with the pump 1216, while another control switch/button may be employed to independently and selectively activate the cutting shaft 1202. Other controls may be provided on the handset 1210 to control other aspects of the tissue resecting system.

Because the motor 1320 is disposed in the footswitch 1300, it can be reused with the footswitch 1300. The flexible drive shaft 1322 can be decoupled from the handset 1210, and because it does not become contaminated by direct contact with fluid and tissue from the patient, it too can be reused. In some cases, the motor 1320 and the flexible drive shaft 1322 may be more costly than the other components of the resector 1200. As such, reusing the motor 1320 and the flexible drive shaft 1322 advantageously reduces the marginal cost of using the tissue resecting system 1010. In some implementations, the footswitch 1300 and/or the flexible drive shaft 1322 may require cleaning/sterilization before they are used again.

Meanwhile, the resector 1200 includes components that come into direct contact with fluid and tissue from the patient. Such components include the cutting element, the cutting shaft 1202, the outflow line 1214, the pump 1216, the connecting line 1217, the filtration system 1218, and the inflow line 1212. After each use, the resector 1200 can be conveniently decoupled from the flexible drive shaft 1322 and discarded, while the same flexible drive shaft 1322 and footswitch 1330 can be coupled to a new resector 1200 for another use. Allowing the resector 1200 to be disposable promotes hygienic use of the tissue resecting system 1010, because it eliminates the need to sterilize the resector 1200 after it has been contaminated. However, allowing the motor 1320 and the flexible drive shaft 1322 to be reused reduces cost, because it does not require all components of the tissue resecting system 1010 to be discarded after only one use. Advantageously, the tissue resecting system 1010 provides the convenience of disposable components while avoiding the costs of a system that requires disposal of more costly components that do not come into direct contact with fluid and tissue from the patient.

As shown in FIG. 7, the footswitch 1300 also includes a user interface 1340 that eliminates the need for a separate user interface, such as the user interface 400 shown in FIG. 6. Like the user interface 400, however, the user interface 1340 allows the user to monitor the operation of the tissue resecting system 1010 and to enter any information required for the tissue resecting process. The user interface 1340 includes a display screen 1342 as well as user inputs 1344 (e.g., pushbuttons, switches, etc.). Alternatively or additionally, the user interface 1340 may include a touch screen. The user may employ the user interface 1340 to set parameters for the control elements 1310 housed in the footswitch 1300. For example, the user may set a cutting speed for the cutting element and/or set a flow rate for the recirculation of fluid through the tissue resecting system 1010. The selected parameters are displayed on the user interface 1340 along with any feedback from the control elements 1310. The information displayed on the user interface 1340 is sufficiently visible even when the footswitch 1300 is placed on the floor for operating the tissue resecting system 1010. Additionally, in some implementations, the user inputs 1344 are designed to be readily operated by the foot of the user. By incorporating the user interface 1340 into the footswitch 1300, even fewer separate components are required for the tissue resecting system 1010. Again, the configuration of the footswitch 1300 makes the tissue resecting system 1010 highly compact, portable, and easy to deploy and operate.

Figure 8:
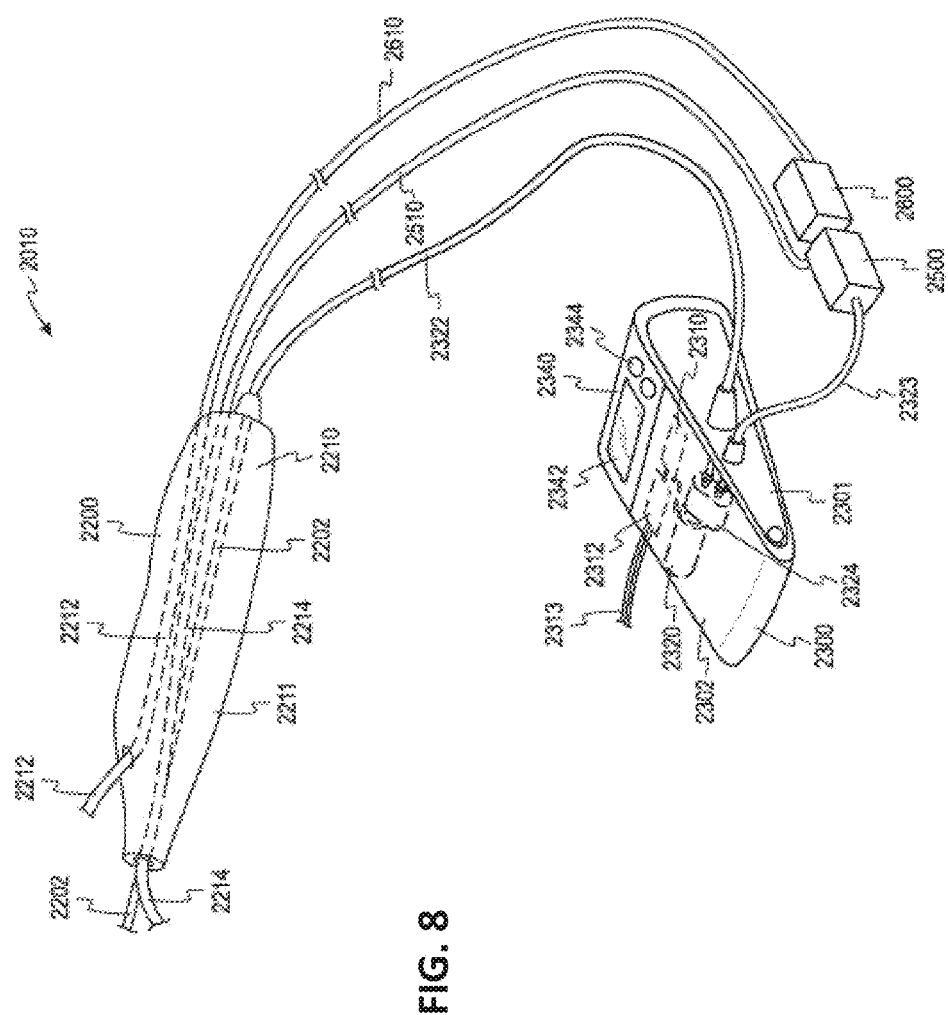
FIG. 8 is a perspective view of yet another a tissue resecting system according to some implementations of the present disclosure.

Referring to FIG. 8, yet another example tissue resecting system 2010 is illustrated. The tissue resecting system 2010 includes a resector 2200, which may be combined with an endoscope (not shown) that is, the same as, or similar to, the endoscope 100 of FIG. 6. The resector 2200 includes a handset 2210 with a housing 2211. The resector 2200 also includes a cutting shaft 2202 that extends distally from the handset 2210 and through the endoscope. The cutting shaft 2202 is employed to generate a cutting action (e.g., translating, rotating, reciprocating, or any combination thereof) with a distal cutting element (not shown), which is positioned within an organ by the endoscope.

Similar to the implementations shown in FIGS. 6 and 7, the handset 2210 includes an outflow line 2214 that receives fluid from the organ and an inflow line 2212 that returns filtered fluid to the organ. As shown in FIG. 8, however, the handset 2210 does not includes a pump or filtration system in the housing 2211. Instead, the tissue resecting system 2010 includes a pump 2500 and a filtration system 2600 that are separate components disposed outside the housing 2211. The pump 2500 is coupled to the handset 2210 via a pump line 2510. The pump line 2510 is removably coupled to a proximal end of the handset 2210 where it is connected to the outflow line 2214, which extends through the housing 2211 of the handset 2210. The pump 2500 is capable of producing sufficient suction to draw the fluid from the organ and through the outflow line 2214 and the pump line 2510. The pump 2500 may be a positive displacement pump, such as a gear pump, a diaphragm pump, a peristaltic pump, a cavity pump, a lobe pump, a piston pump, or the like. The magnitude of suction depends on the cutting device, tissue nature, and the hydraulic resistance in the extraction path.

The pump 2500 is coupled to the filtration system 2600. Accordingly, the fluid from the outflow line 2214 is drawn through the pump line 2510 by the pump 2500 and to the filtration system 2600. The filtration system 2600 includes a filter/tissue trap that removes the tissue and other material from the fluid received by the handset 2210. The filter/tissue trap may be removable or otherwise accessible to allow the tissue from the organ to be collected and examined. The filtration system 2600 is coupled to the handset 2210 via a filtration system line 2610. The filtration system line 2610 is removably coupled to the proximal end of the handset 2210 where it is connected to the inflow line 2212, which also extends through the handset 2210. The filtration system line 2610 allows filtered fluid to be returned to the inflow line 2212 and to the organ via an endoscope as described above.

Additionally, the tissue resecting system 2010 includes a footswitch 2300. The footswitch includes a motor 2320 to drive the pump 2500 as well as the cutting shaft 2202 to generate the cutting action with the cutting element. The fluid flow from the pump 2500 can be controlled independently from the cutting operation with the cutting shaft 2202. Thus, the footswitch 2300 includes a gear box and clutch 2324 that divides the drive from the motor 2320 between the pump 2500 and the cutting shaft 2202. The gear box and clutch 2324 is coupled to and drives the pump 2500 via a flexible pump drive shaft 2323. The flexibility of the pump drive shaft 2323 provides sufficient freedom of motion to permit the pump 2500 to be conveniently positioned relative to the footswitch 2300.

The gear box and clutch 2324 is coupled to and drives the cutting shaft 2202 via a flexible cutting drive shaft 2322. The flexible cutting drive shaft 2322 is removably coupled to the proximal end of the handset 2210 where it is connected to the cutting shaft 2202, which extends through the housing 2011 of the handset 2210. The flexibility of the drive shaft 2322 provides sufficient freedom of motion to permit the resector 2200 to be freely manipulated.

The footswitch 2300 includes a body 2301 with an upper surface 2302. The user applies a force against the upper surface 2302 (e.g., with his/her foot) to operate the footswitch 2300. Mechanical action resulting from the force against the upper surface 2302 generates an electrical signal that delivers power to and drives the motor 2320, which in turn drives the flexible cutting drive shaft 2322 and the flexible pump drive shaft 2323. The footswitch 2300 also includes control elements 2310 (e.g., one or more PCB assemblies with one or more processors). In particular, the control elements 2310 allow the motor 2320 and thus the flexible cutting drive shaft 2322 and the flexible pump drive shaft 2323 to be driven according to selected parameters, such as revolutions per minute (RPM), which in turn determine how the cutting shaft 2202 and the pump 2500 operate. The footswitch 2300 is selectively operated by the user to engage the gear box and clutch 2324 to deliver drive to the flexible cutting drive shaft 2322 and the flexible pump drive shaft 2323. As shown in FIG. 8, the footswitch 2300 receives electrical power from an external source via an electrical cable 2313 and includes an electrical transformer 2312 to convert the main electrical supply into suitable voltages for powering and controlling aspects of the tissue resecting system 2010.

The footswitch 2300 also includes a user interface 2340 that eliminates the need for a separate user interface, such as the user interface 400 shown in FIG. 6. Like the user interface 1340 described above, the user interface 2340 allows the user to monitor the operation of the tissue resecting system 2010 and to enter any information required for the tissue resecting process (e.g., set parameters for the control elements 2310 housed in the footswitch 2300). The user interface 2340 includes a display screen 2342 as well as user inputs 2344 (e.g., pushbuttons, switches, etc.). Alternatively or additionally, the user interface 2340 may include a touch screen.

Like the motor 1320 and the flexible drive shaft 1322 described above, the motor 2320, the flexible drive shaft 2322, and the flexible pump drive shaft 2323 can be reused, while other components that come into direct contact with fluid and tissue from the patient can be conveniently discarded after a single use. Such disposable components include the resector 2200, the pump 2500, the pump line 2510, the filtration system 2600, and the filtration system line 2610. Allowing these components to be disposable promotes hygienic use of the tissue resecting system 2010, because it eliminates the need to sterilize the components after they have been contaminated. After each use of the tissue resecting system 2010, the resector 2200, and the pump 2500 can be conveniently decoupled from the flexible cutting drive shaft 2322 and the flexible pump drive shaft 2323 and discarded along with the pump line 2510, the filtration system 2600, and the filtration system line 2610. Meanwhile, the same footswitch 2300, the flexible cutting drive shaft 2322, and the flexible pump drive shaft 2323 can be coupled to a new resector 2300, pump 2500, filtration system 2600, etc., for another use. Allowing the motor 2320, the flexible cutting drive shaft 2322, and the flexible pump drive shaft 2323 to be reused reduces the marginal cost of using the tissue resecting system 2010.

Because the pump 2500 and the filtration system 2600 are not included in the housing 2211 of the handset 2210, the tissue resecting system 2010 may include more separate components than, for example, the tissue resecting system 1010 described above. The configuration of the resector 2200 is simplified, however, because the handset 2210 only houses the inflow line 2212, the outflow line 2214, and the cutting shaft 2202. The disadvantages of having more separate components in the tissue resecting system 2010 may be offset by the simpler configuration for the resector 2200, which is simpler and less expensive to manufacture. Moreover, with fewer components included in the resector 2200, the resector 2200 is relatively lighter and easier to hold and operate, and further can be completely and thus conveniently discarded after a single use.

Figure 9:
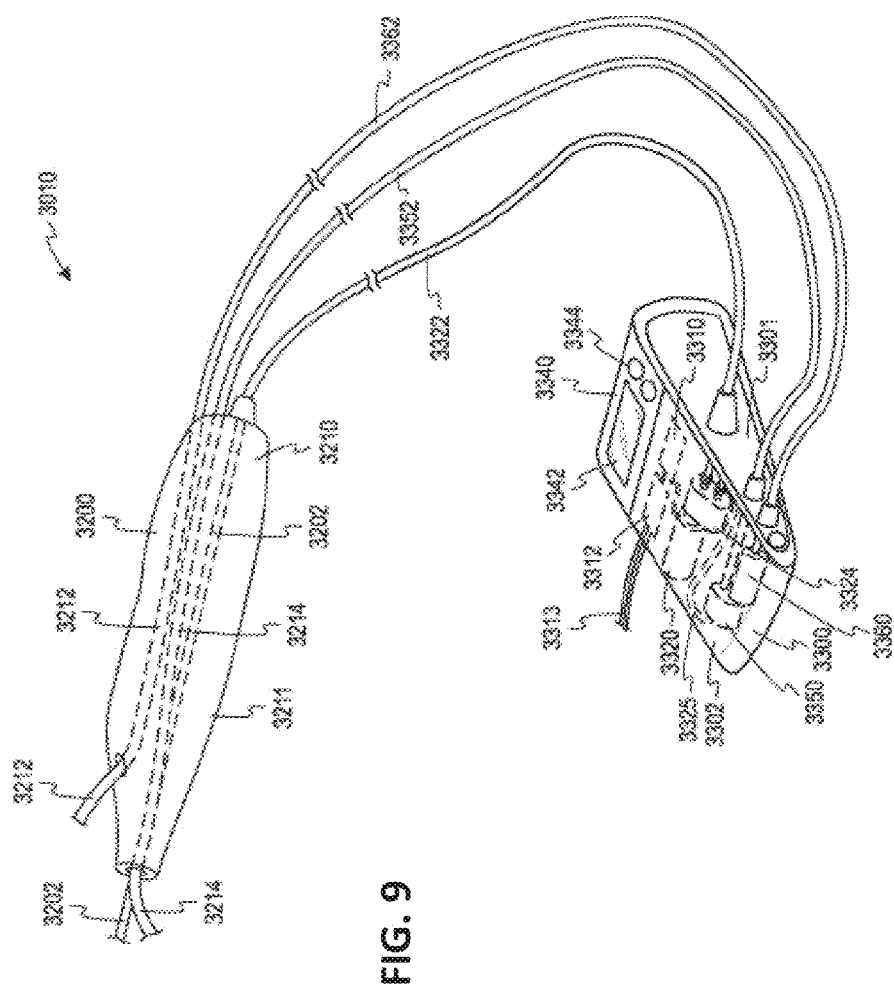
FIG. 9 is a perspective view of a further tissue resecting system according to some implementations of the present disclosure.

Referring to FIG. 9, a further example tissue resecting system 3010 is illustrated. The tissue resecting system 3010 includes a resector 3200, which may be combined with an endoscope (not shown) that is the same as, or similar to, the endoscope 100 of FIG. 6. The resector 3200 includes a handset 3210 with a housing 3211. The resector 3200 also includes a cutting shaft 3202 that extends distally from the handset 3210 and through the endoscope. The cutting shaft 3202 is employed to generate a cutting action (e.g., translating, rotating, reciprocating, or any combination thereof) with a distal cutting element (not shown), which is positioned within an organ by the endoscope.

The handset 3210 includes an outflow line 3214 that receives fluid from the organ and an inflow line 3212 that returns filtered fluid to the organ. Similar to the handset 2210 shown in FIG. 8, the handset 3210 does not include a pump or filtration system in the housing 3211. Instead, the tissue resecting system 3010 includes a footswitch 3300 that houses a pump 3350 and a filtration system 3360 separately from the handset 3210.

The pump 3350 is coupled to the handset 3210 via a pump line 3352. The pump line 3352 is removably coupled to a proximal end of the handset 3210 where it is connected to the outflow line 3214, which extends through the housing 3211 of the handset 3210. The pump 3350 is capable of producing sufficient suction to draw the fluid from the organ and through the outflow line 3214 and the pump line 3352. The pump 3350 is sufficiently compact to permit the footswitch 3300 to have a convenient size and shape for easy operation. The pump 3350 may be a positive displacement pump, such as a gear pump, a diaphragm pump, a peristaltic pump, a cavity pump, a lobe pump, a piston pump, or the like. The magnitude of suction depends on the cutting device, tissue nature, and the hydraulic resistance in the extraction path.

The pump 3350 is coupled to the filtration system 3360. Accordingly, the fluid from the outflow line 3214 is drawn through the pump line 3352 by the pump 3350 and to the filtration system 3360. The filtration system 3360 includes a filter/tissue trap that removes the tissue and other material from the fluid received through the handset 3210. The filter/tissue trap may be removable or otherwise accessible to allow the tissue from the organ to be collected and examined. The filtration system 3360 is coupled to the handset 3210 via a filtration system line 3362. The filtration system line 3362 is removably coupled to the proximal end of the handset 3210 where it is connected to the inflow line 3212 which also extends through the housing 3211 of the handset 3210. The filtration system line 3362 allows filtered fluid to be returned to the inflow line 3212 and to the organ via an endoscope as described above.

The footswitch 3300 also includes a motor 3320 to drive the pump 3350 and the cutting shaft 3202 to generate the cutting action with the cutting element. The fluid flow from the pump 3350 can be controlled independently from the cutting operation with the cutting element. Thus, the footswitch 3300 includes a gear box and clutch 3324 that divides the drive from the motor 3320 between the pump 3350 and the cutting shaft 3202. The gear box and clutch 3324 is coupled to and drives the pump 3350 via a pump drive coupling 3325. As shown in FIG. 9, the drive coupling 3325 may be a flexible drive shaft to allow the components in the footswitch 3300 to be compactly arranged, but it is understood that other structures for transmitting the drive from the motor 3320 to the pump 3350 may be employed.

The gear box and clutch 3324 is also coupled to and drives the cutting shaft 3202 via a flexible cutting drive shaft 3322. The flexible cutting drive shaft 3322 is removably coupled to the proximal end of the handset 3210 where it is connected to the cutting shaft 3202 which extends through the housing 3211 of the handset 3210. The flexibility of the drive shaft 3322 provides sufficient freedom of motion to permit the resector 3200 to be freely manipulated.

The footswitch 3300 includes a body 3301 with an upper surface 3302. The user applies a force against the upper surface 3302 (e.g., with his/her foot) to operate the footswitch 3300. Mechanical action resulting from the force against the upper surface 3302 generates an electrical signal that delivers power to and drives the motor 3320, which in turn drives the flexible drive shaft 3322 and the pump drive coupling 3325. The footswitch 3300 includes control elements 3310 (e.g., one or more PCB assemblies with one or more processors). In particular, the control elements 3310 allow the motor 3320 and thus the flexible drive shaft 3322 and the pump drive coupling 3325 to be driven according to selected parameters, such as revolutions per minute (RPM), which in turn determine how the cutting shaft 3202 and the pump 3250 operate. The footswitch 3300 is selectively operated by the user to engage the gear box and clutch 3324 to drive the flexible drive shaft 3322 and the pump drive coupling 3325. As shown in FIG. 9, the footswitch 3300 receives electrical power from an external source via an electrical cable 3313 and includes an electrical transformer 3312 to convert the main electrical supply into suitable voltages for powering and controlling of aspects of the tissue resecting system 3010.

The footswitch 3300 also includes a user interface 3340 that eliminates the need for a separate user interface, such as the user interface 400 shown in FIG. 6. Like the user interfaces 1340 and 2340 described above, the user interface 3340 allows the user to monitor the operation of the tissue resecting system 3010 and to enter any information required for the tissue resecting process (e.g., set parameters for the control elements 3310 housed in the footswitch 3300). The user interface 3340 includes a display screen 3342 as well as user inputs 3344 (e.g., pushbuttons, switches, etc.). Alternatively or additionally, the user interface 3340 may include a touch screen.

The resector 3200, the pump 3350, the pump line 3352, the filtration system 3360, and the filtration system line 3362 come into direct contact with fluid and tissue from the patient. Conveniently, the resector 3200, the pump line 3352, and the filtration system line 3362 can be decoupled from the footswitch 3300 and completely discarded after a single use. The footswitch 3300, however, houses the pump 3350 and the filtration system 3360 with other components that do not come into direct contact with fluid and tissue from the patient. Thus, the footswitch 3300 is configured to allow the pump 3350 and the filtration system 3360 to be removed and discarded after single use, while the rest of the footswitch 3300 can be reused with a new pump 3350 and a new filtration system 3360.

The footswitch 3300 may be defined by separable disposable and reusable portions. The disposable portion includes the pump 3350 and the filtration system 3360. Meanwhile, the reusable portion includes the control elements 3310, the electrical transformer 3312, the motor 3320, the gear box and clutch 3324, the user interface 3340, etc., which can be used more than one time. These reusable components are sometimes more costly. In some implementations, the disposable portion may be configured as a removable cartridge intended to be discarded after only one use. The removable cartridge may be detachably coupled to the rest of the footswitch 3300. After each use, the disposable cartridge is detached and discarded. Each disposable cartridge may be individually and sterilely packaged.

Allowing components, such as the pump 3350 and the filtration system 3360, to be easily removed for disposal promotes hygienic use of the tissue resecting system 3010, because it eliminates the need to sterilize such components after they have been contaminated. Meanwhile, allowing other components to be reused reduces cost, because it does not require all components of the tissue resecting system 3010 to be discarded after only one use. Advantageously, the tissue resecting system 3010 provides the convenience of disposable components while avoiding the costs of a completely disposable system. Accordingly, the footswitch 3300 contains many of the components required for cutting and extracting tissue from an organ and recirculating fluid through the organ. By incorporating the control elements 3310, the user interface 3340, the pump 3350, the filtration system 3360, etc., into the footswitch 3300, the tissue resecting system 3010 reduces the number of separate components that would have to be assembled and organized for a procedure. In general, the tissue resecting system 3300 can perform a procedure with three basic components: an endoscope (e.g., the endoscope 100 shown in FIG. 6), the resector 3200, and the footswitch 3300.

In addition, by incorporating many components into the footswitch 3300, the configuration of the resector 3200 is simplified as the handset 3210 only houses the inflow line 3212, the outflow line 3214, and the cutting shaft 3202. The simplified resector 3300 may be simpler and less expensive to manufacture. Moreover, with fewer components included in the resector 3200, the resector 3200 is relatively lighter and easier to hold and operate, and further can be completely and thus conveniently discarded after a single use.

Figure 10:
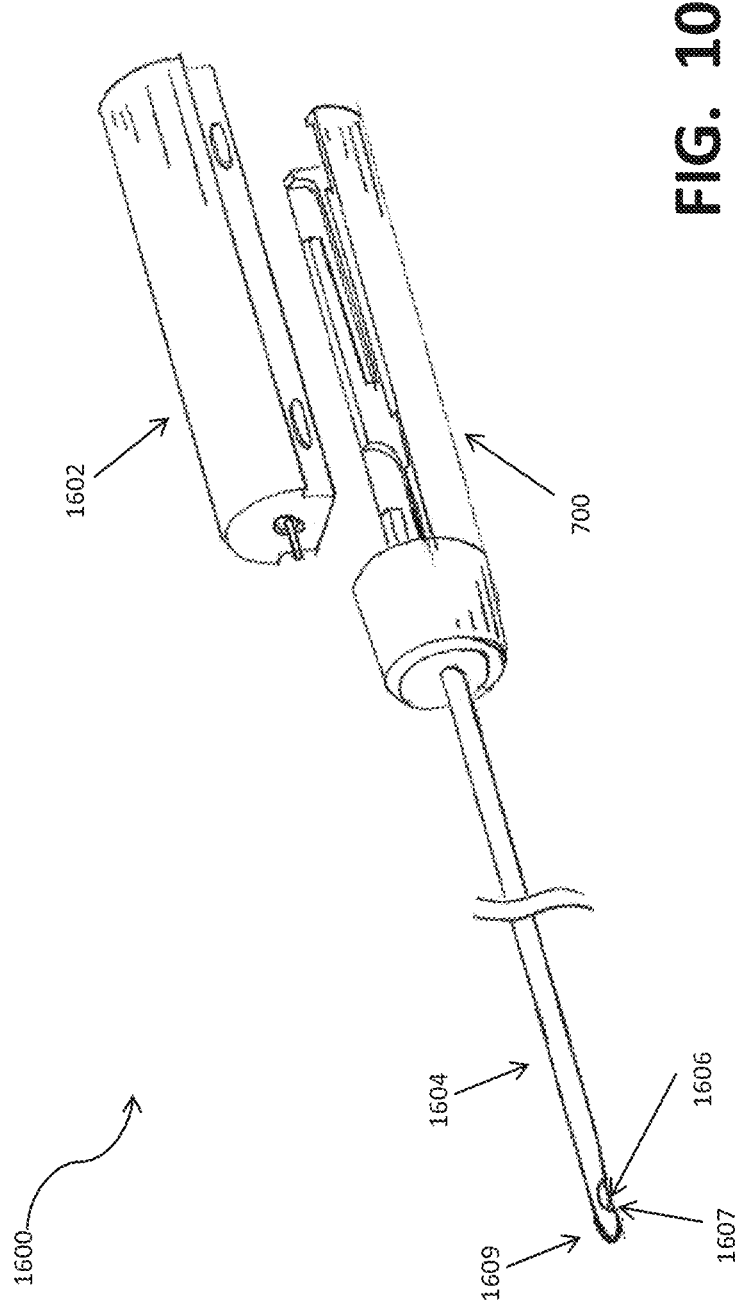
FIG. 10 is a perspective view of a tissue resecting handset that comprises a reusable component and a disposable portion.

FIG. 10 is a perspective view of a tissue resecting handset 1600 that comprises a reusable portion 1602 and a disposable portion 700 in accordance with yet still other embodiments. The handset 1600 may be coupled to a plurality of peripheral devices including a power source, fluid source, filtration device, and pump, as discussed below in detail in FIGS. 11-14. The handset 1600 is configured so that the reusable portion 1602 and the disposable portion 700 are engaged along a plurality of locking features on each portion and disengaged after use, at which point the disposable portion is disposed and the reusable portion is either cleaned but not sterilized, or cleaned and sterilized, depending upon the embodiment and configuration of the handset 1600. The handset may comprise an elongated shaft 1604 having an aperture 1607 at a distal end 1609 of the elongated shaft 1604. A cutting element 1606 is disposed within the elongated shaft 1604 in operational relationship to the aperture 1607.

Figure 11A:
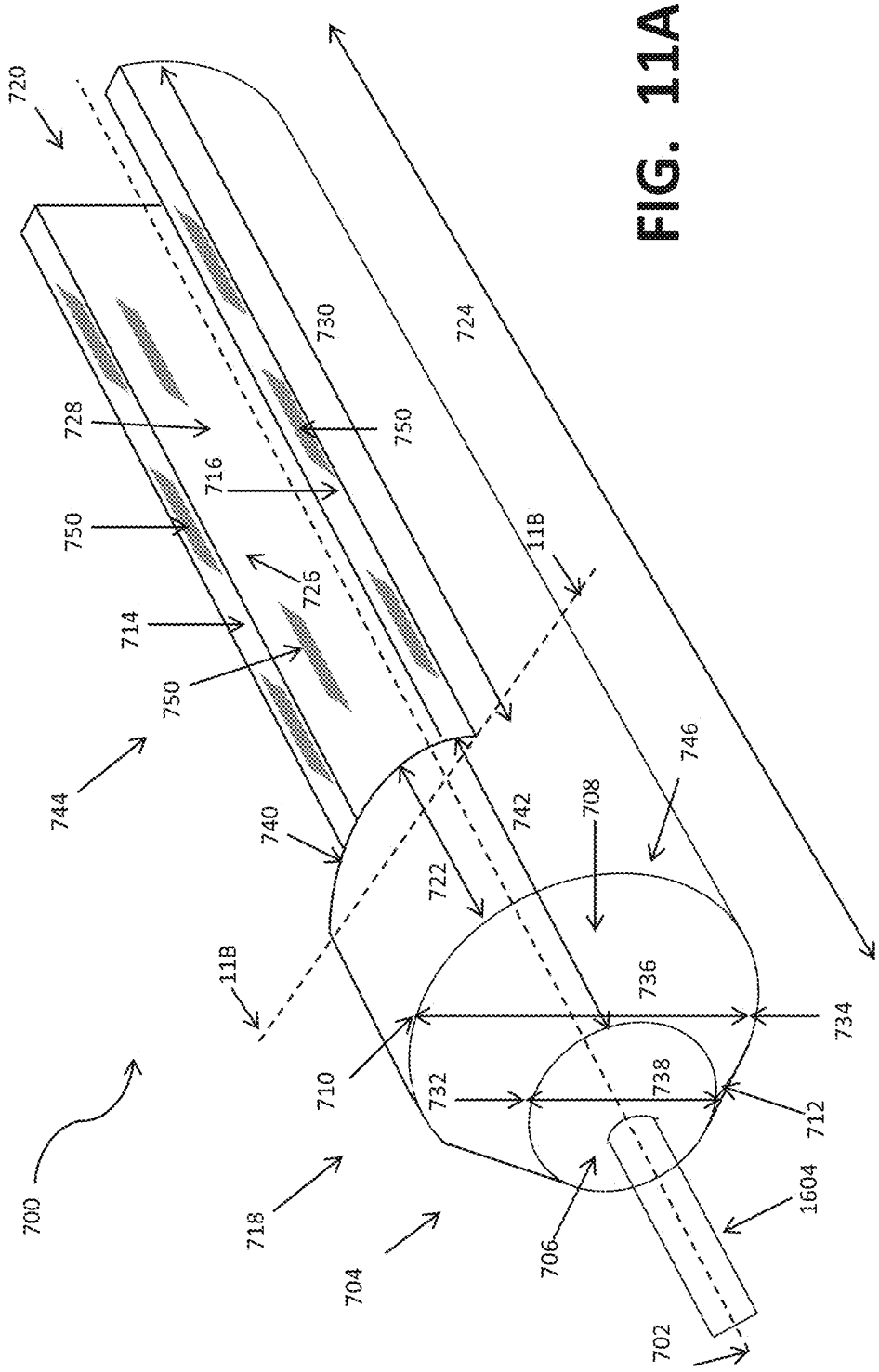
FIG. 11A is a partial perspective view of a disposable portion of a handset.

FIG. 11A is a partial perspective view of a disposable portion 700 of a handset. In an embodiment, the disposable portion 700 comprises a central axis 702, a tapered distal end of the handle portion 704 and a proximal end 720. The disposable portion 700 further comprises an overall length 724 comprising a first portion 718 and a second portion 744, the first portion 718 comprising a length 742, the first portion 718 may also be referred to as the hub section 718 since a rotational hub is disposed in the hub section (the rotational hub is illustrated and discussed below in at least FIGS. 14A and 14B). The distal end of the hub section 718 comprises an instrument engagement feature 706 where an elongated shaft comprising a cutting element may be disposed (only a portion of the elongated shaft is visible). The tapered distal end of the handle portion 704 is defined by a first elliptical feature 712 comprising a largest outer diameter 736 and a second elliptical feature 746 comprising a largest outer diameter 738, a length 742, and a smooth transition surface 708 between the first 712 and the second elliptical feature 746 circumferentially around the hub section 718. The distal end of the hub section 718 may be defined in various configurations and geometries. In an embodiment, the distal end of the hub section 718 may be further defined by an apex 710 and a bottom smoothly curved surface 734, both along the second elliptical feature 746, and an apex 732, and an elongated shaft 1604 that is in communication with a fluid path within the hub portion 718, not shown here. The hub section 718 comprises a proximal portion length 722 and a proximal end 740 configured to mate with a reusable portion (not pictured) via a plurality of locking features. The second portion 744 comprises a length 730, a first surface 714, and a second surface 716, and may also be referred to as the mating section 744. The first 714 and second 716 surfaces extend from the proximal end 740 of the hub section 718 to the proximal end 720 of the disposable portion 700 parallel to the central axis 702. While the mating section 744 is illustrated here in one embodiment, in alternate embodiments, it may be different in length or otherwise vary as appropriate for the design of the disposable portion 700.

In an embodiment, a channel 728 extends for at least a portion of the mating section 744. The mating section 744 may comprise a plurality of locking features 750, which may be formed and/or disposed on any or all of the first surface 714, the second surface 716, and/or an interior surface 726 of the channel 728. The plurality of locking features 750 may be disposed in various patterns, configurations using varying geometries and styles. The plurality of locking features 750 may comprise guide tracks (as shown in FIG. 10), rails, press-fit features, snap-fit features, pins, fasteners, frictional engagement, threads, or combinations thereof as appropriate. The elongated shaft 1604 may extend beyond that shown in FIG. 11A and may comprise the cutting element 1606 (FIG. 10), and in some embodiments as shown above the elongated shaft 1604 may be telescoped through the working channel of an endoscope. The elongated shaft 1604 engages with a fluid channel (not shown here) that extends through both the hub section and the mating section of the disposable portion 700, and fluid and/or tissue are resected and drawn from an organ through the elongated shaft 1604, into the fluid channel through the disposable portion 700 to the proximal end 720. The proximal end 720 may be configured to fluidly couple at least to a waste, collection, filtration, or other apparatus configured to receive at least one of fluid and/or tissue removed from the organ.

Figure 11B:
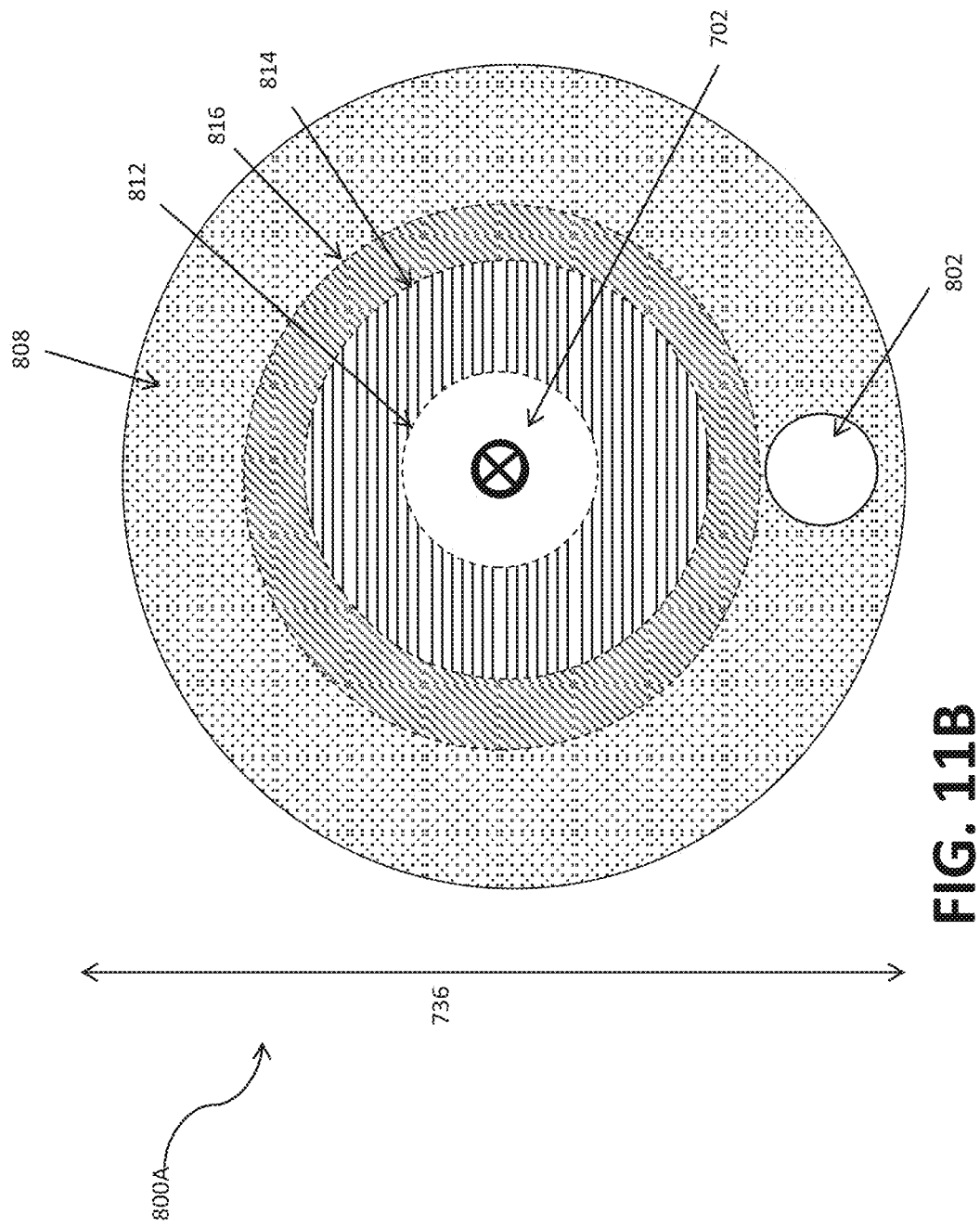
FIG. 11B is a cross sectional view of a disposable portion of a handset taken substantially along line 11B-11B in FIG. 11A.

FIG. 11B is a cross sectional view 800A taken along line 11B-11B in FIG. 11A. In particular, FIG. 11B illustrates the central axis 702, fluid path 802 through the hub section. The fluid path 802 may comprise a consistent diameter throughout, or may be tapered, depending upon the embodiment. FIG. 11B also illustrates a driver connector 812, in some embodiment in the form of a counter-bore into the rotating hub 814 into which a hub drive shaft of the reusable portion (discussed below) telescopes as part of being detachably connected. Also visible is the rotating hub 814, which may be fluidly isolated from the reusable portion by a seal 816, which may comprise an o-ring, a shaft seal, or a spring seal.

FIG. 12 is a perspective view 900 of the disposable portion 700, illustrated from the proximal end 720 looking towards the distal end in order to illustrate the locking and other mating features. The view 900 illustrates the central axis 702, and a rotating hub 814 is disposed in the hub portion 718 exposed to the mating section. The rotating hub 814 defines the driver connector 812, in some embodiment in the form of a counter-bore into the rotating hub 814. Also illustrated in the view 900 are a third flat surface 902 located on the proximal end 740 of the hub section 718, and the third flat surface 902 may comprise a plurality of locking features 750 as discussed above. The seal 816 is not illustrated in this view, as the rotating hub 814 is only partially exposed in this embodiment. Also illustrated are the additional locations for locking features 750, including the interior surface 726 of the channel 728, the first surface 714 extending from the proximal end 740 of the hub portion 718 to the proximal end 720 on the first side 908 and comprising a width 904, and the second surface 716 extending from the proximal end 740 of the hub portion 718 to the proximal end 720 on a second side 910 and comprising a width 906.

Figure 13A:
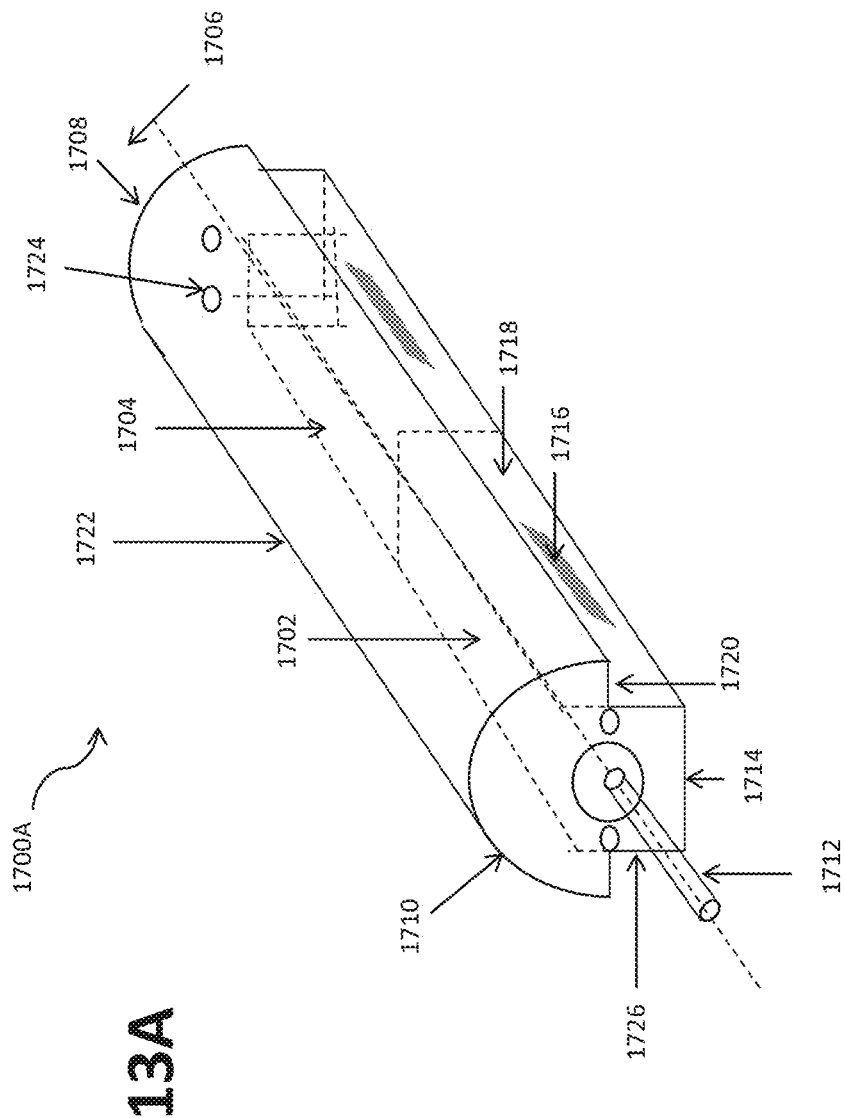
FIGS. 13A and 13B are schematic illustrations of a perspective view (FIG. 13A) and an end elevation view (FIG. 13B) of a reusable portion of a handset.
Figure 13B:
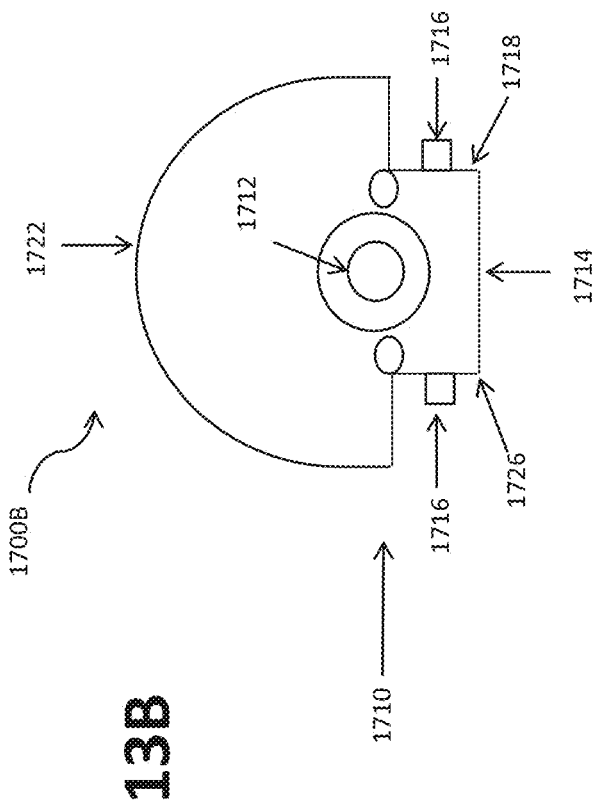
Figure 14A:
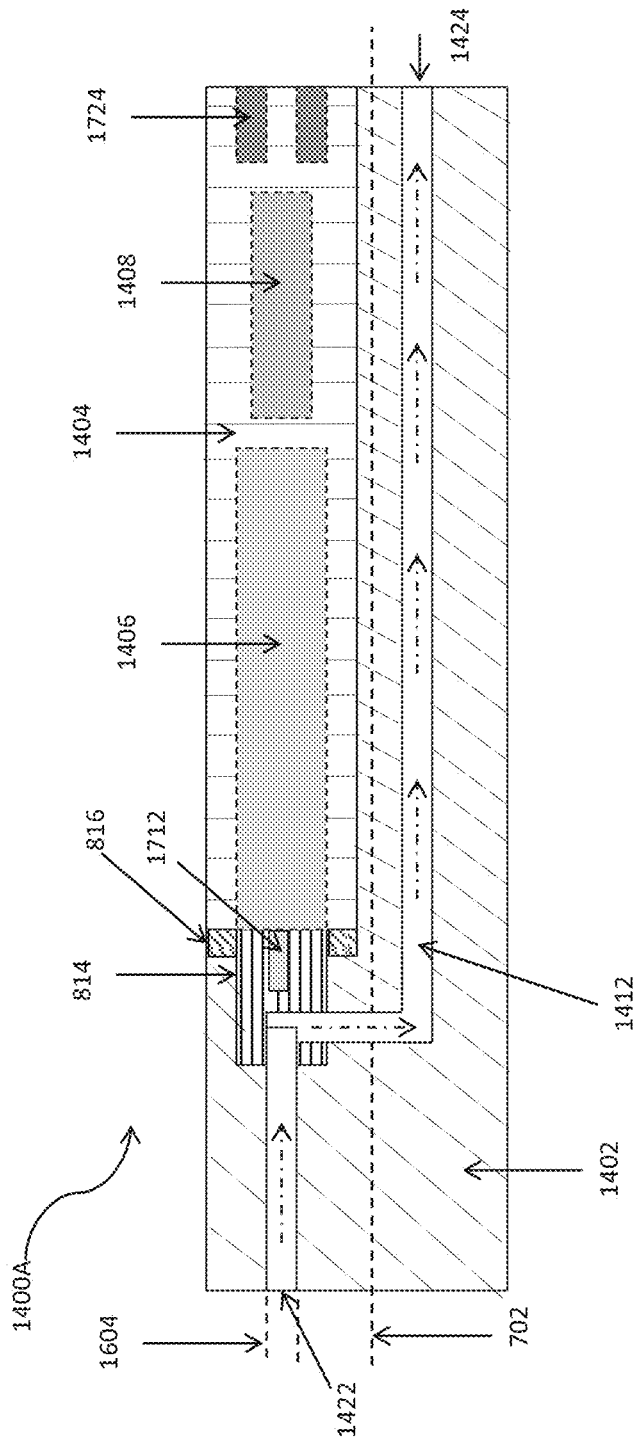
FIGS. 14A-14B illustrate different schematic cross sectional views of the disposable portion of a handset detachably coupled to a reusable portion of the handset according to embodiments of the present disclosure.
Figure 14B:
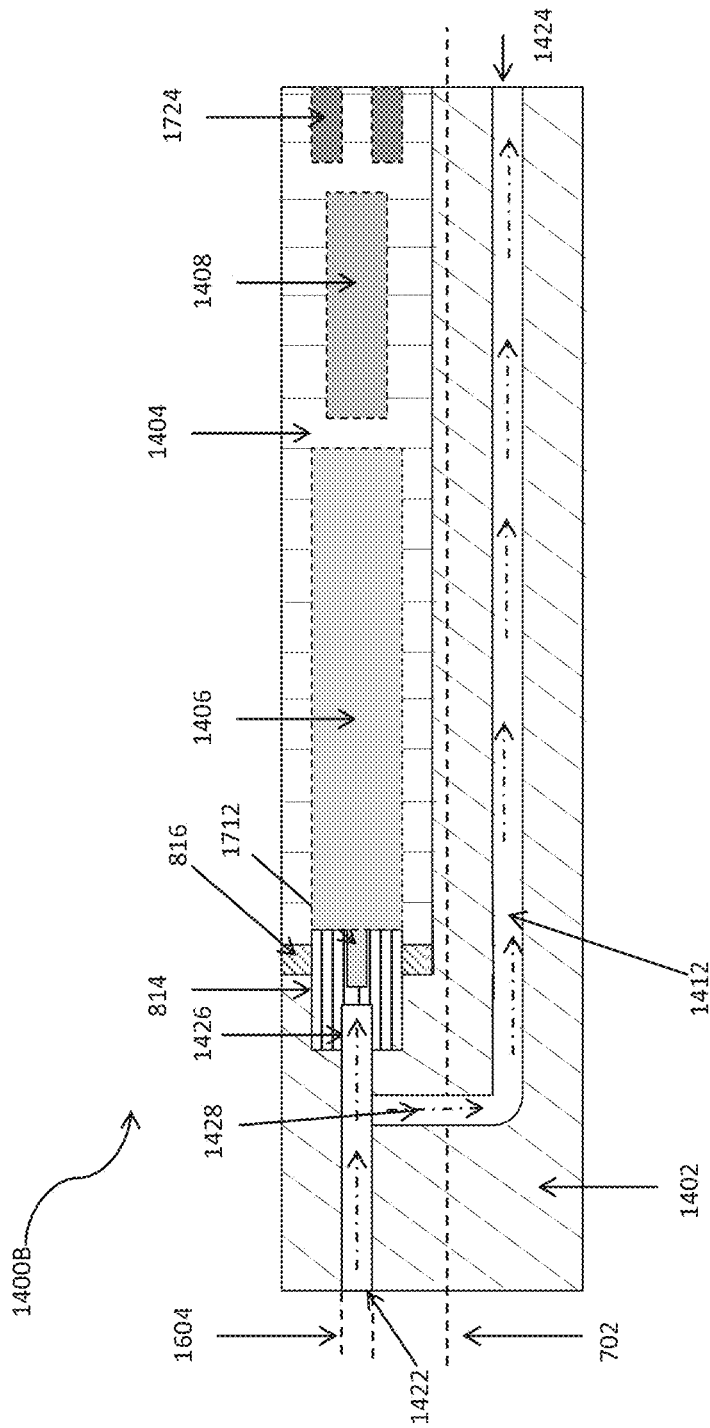

FIGS. 13A and 13B are schematic illustrations of a perspective view 1700A (FIG. 13A) and an end elevation view 1700B (FIG. 13B) of a reusable portion of a handset. FIG. 13A illustrates the perspective view 1700A of the reusable portion, which comprises an outer casing defined by a smoothly curved upper surface 1722, a first side 1718 and a second side 1726 that are parallel to the central axis 1706. The smoothly curved upper surface 1722 joins the first side 1718 and the second side 1726 by way of shelves 1720 (the shelves 1720 are perpendicular to their respective sides 1718 and 1726). In an embodiment, the example reusable portion also comprises a bottom feature that may be a flat bottom feature 1714 perpendicular to the sides 1718 and 1726. The outer casing extends along a length from a distal end 1710 to a proximal end 1708 along a central axis 1706. The reusable portion 1700A comprises a motor and a heat sink 1702 as well as a plurality of electronic components 1704 and at least one connection port 1724 that may be used to supply power to the reusable portion and/or to connect to peripheral devices. The motor 1702 and the plurality of electronic components 1704 may be in various configurations disposed adjacent to one another or spaced a predetermined distance from each other, depending upon the embodiment. The motor 1702 may comprise a hub drive shaft 1712 that extends from the motor 1702 at the distal end 1710, parallel to the central axis 1706. When the reusable portion is coupled to the mating section of disposable portion, the hub drive shaft 1712 couples to the rotating hub of the disposable portion, as illustrated in FIGS. 14A and 14B. The reusable portion shown in view 1700A may further comprise a plurality of locking features 1716 formed on at least one of the sides 1726 and 1718. In some embodiments, the shelves 1720 are parallel to both the central axis 1706 and perpendicular to the sides 1726 and 1718, and may comprise locking features (which are not visible in the view of FIG. 13A). The locking features 1716 may comprise tabs (such as shown in FIG. 10), guide rails, press-fit features, snap-fit features, pins, fasteners, frictional engagement, threads, or combinations thereof as appropriate, and are configured to mate with some or all of the plurality of locking features 750 discussed in FIGS. 10-12.

FIG. 13B is the end-elevation view 1700B of the distal end 1710 of 1700A from FIG. 13A, and illustrates the outer casing's curved top surface 1722, flat bottom 1714, the hub drive shaft 1712 of the motor (not pictured in FIG. 13B), the first and second sides 1718 and 1726 where the locking features 1716 may be located.

FIGS. 14A-14B illustrate different schematic cross sectional views of the disposable portion of a handset detachably coupled to a reusable portion of the handset according to embodiments of the present disclosure. In particular, FIG. 14A is an illustration of a partial cross section 1400A of an embodiment of the disposable portion of a handset detachably coupled to a reusable portion of the handset. The cross section 1400A illustrates a disposable portion 1402 and a reusable portion 1404. The disposable portion 1402 comprises the fluid path 1412 which begins in an instrument, partially shown in FIG. 14A as elongated shaft 1604 (as also shown in FIG. 10), and, as discussed above, has an inflow location 1422 and an outflow location 1424. In the example embodiment shown, the fluid path 1412 extends into and through the rotating hub 814 and continues through the disposable portion 1402. The fluid path 1412 in FIG. 14B extends into the rotating hub to enable the blade drive shaft (not specifically shown) to access the fluid path, and the rotating hub is designed and constructed to enable the fluid and/or resected tissue to travel through the hub. The seal 816 may comprise an O-ring or another type of seal, which may be a flexible or a rigid seal, or comprise multiple components, may be disposed on an outside surface of the rotating hub 814, and particularly on the proximal side of the rotating hub 814. The seal 816 fluidly isolates the rotating hub 814 (and the disposable portion 1402) from the motor 1406, electronics 1408, and other components in the reusable portion 1404, which may also comprise at least one connection port 1724 for power and other connections. The reusable portion 1404 may be detachably coupled to the detachable portion 1402 by multiple means including the locking features 750 discussed above, which are engaged but not illustrated in this view, as well as through the coupling of the hub drive shaft 1712 extending from the motor 1406 that mates with a drive connector defined in the rotating hub 814 as illustrated.

FIG. 14B is an illustration of a partial cross section 1400B of an embodiment of the disposable portion of a handset detachably coupled to a reusable portion of the handset. The cross section 1400B illustrates a disposable portion 1402 and a reusable portion 1404. The disposable portion 1402 comprises the fluid path 1412 which begins in an instrument, partially shown in FIG. 14A as the elongated shaft 1604, and, as discussed above, has an inflow location 1422 and an outflow location 1424. The fluid path 1412 extends to but not through the rotating hub 814, and fluid path also extends through the disposable portion 1402. The fluid path 1412 in FIG. 14B extends to the rotating hub to enable the blade drive shaft (not specifically shown) to access the fluid path. However, in the example system of FIG. 14B the fluid path 1412 does not extend through the rotating hub 814. The portion 1428 of the fluid path is illustrated as being oriented perpendicular to the central axis 702, but in some embodiments, it may be angled towards the outflow location 1424. As discussed above in FIG. 14A, seal 816, which may comprise an O-ring or another type of seal, which may be a flexible or a rigid seal, or comprise multiple components, may be in operational relationship to the rotating hub 814 and fluidly isolates the rotating hub 814 (and the disposable portion 1402) from the motor 1406, electronics 1408, and other components in the reusable portion 1404, which may also comprise at least one connection port 1724 for power and other connections. The reusable portion 1404 may be detachably coupled to the detachable portion 1402 by multiple means including the locking features 750 discussed above, which are engaged but not illustrated in this view, as well as through the coupling of the hub drive shaft 1712 from the motor 1406 that mates with the rotating hub 814 as illustrated.

FIG. 15 illustrates a system diagram for a tissue resecting system 1500 according to certain embodiments of the present disclosure. The system 1500 comprises a foot switch 1502 coupled to a power source 1504 that is also coupled to a pump/suction device 1506, a filtration device 1508, and a fluid source 1512. The power source 1504 is also coupled to the handset 1510 that comprises the disposable portion discussed above and, in some cases, an endoscope 1514. The handset 1510 may also be coupled to the filtration device 1508 by way of tubing, and the filtration device 1508 may be connected to a sample collection station which the handset 1510 may in some cases directly access without filtration using 1508. The power source 1504 may supply power to the handset 1510 for at least the motor to activate the cutting device, which may also be coupled to the pump/suction device 1506 to provide suction through the fluid channel while cutting tissue and removing fluid. The handset 1510 may be connected to one or both of the filtration 1508 and sample collection 1516 devices and may use one or both depending upon the embodiment (as indicated by the arrows) in order to collect tissue samples and recirculate the fluid as illustrated, where the fluid is removed by the handset 1510, sent through the filtration device 1508, where the tissue is separated out, and then the fluid may be returned (recirculated) to the body, for example, by way of the endoscope 1514. After the procedure is finished, the disposable portion of the handset 1510 may be disengaged from the reusable portion and disposed of, while the reusable portion is wiped manually or otherwise cleaned, in some embodiments the reusable portion is not sterilized, for example, using an autoclave, and in other embodiments sterilization may be employed. In an embodiment, the endoscope 1514 may be in fluid communication with the sample collection device 1516, and in other embodiments (not illustrated here), the endoscope may be connected to the filtration device 1508 directly, e.g., not through the handset portion, in addition to or instead of the connection to the sample collection device 1516.

In an embodiment, tissue resecting system, comprising: a resector including a handset and a cutting element that extends from the handset to cut tissue from an organ; and a footswitch coupled to the resector, the footswitch being selectively operated to activate the cutting element, and the footswitch including one or more control elements that control the operation of the cutting element according to selected parameters. The tissue resecting system of claim 1, wherein the footswitch includes a motor that is coupled to and drives the cutting element via a flexible drive shaft, the one or more control elements controlling the motor to drive the cutting element. The tissue resecting system further comprising wherein the handset includes a pump, a first fluid line, and a second fluid line, the pump drawing fluid, with suction, from the organ through the first fluid line and pushing the fluid into the second fluid line for further processing, and the fluid drawn from the organ by the pump carries tissue cut from the organ by the cutting element, the footswitch being selectively operated to activate the pump, the one or more control elements controlling the operation of the pump according to the selected parameters. The tissue resecting system further comprising wherein the handset includes a filtration system that filters the fluid from the organ, the pump pushing the fluid through the filtration system and into the second fluid line, the second fluid line delivering the filtered fluid to the organ. The tissue resecting system further comprising an endoscope that is configured to be inserted into the organ and to guide the cutting element into the organ, the endoscope including a passageway that is configured to extend into the organ, the passageway being coupled to the second fluid line, the passageway delivering the filtered fluid to the organ. In an embodiment, the footswitch includes a motor that is coupled to a gear box and clutch component via a flexible drive shaft, the gear box and clutch component driving the cutting element and the pump, the one or more control elements controlling the motor to drive the cutting element and the pump according to the selected parameters. In an embodiment, a pump may be disposed externally from the handset, wherein the handset include a first fluid line and a second fluid line, the pump drawing fluid, with suction, from the organ through the first fluid line and pushing the fluid into the second fluid line for further processing, the fluid drawn from the organ by the pump carrying tissue cut from the organ by the cutting element, the footswitch being selectively operated to activate the pump, the one or more control elements controlling the operation of the pump according to the selected parameters, and in some embodiments, the pump is housed in the footswitch. The footswitch includes a motor that is coupled to a gear box and clutch component via a flexible drive shaft, the gear box and clutch component driving the cutting element and the pump, the one or more control elements controlling the motor to drive the cutting element and the pump according to selected parameters.

In an embodiment, filtration system may be disposed externally from the handset, the filtration system filtering the fluid from the organ, the pump pushing the fluid through the filtration system and into the second fluid line, the second fluid line delivering the filtered fluid to the organ, and in some embodiments, the filtration system is housed in the footswitch. The footswitch includes a user interface, the user interface including a display and user inputs, the user inputs receiving the selected parameters from a user. In an embodiment, a first pump is disposed externally from the handset and a second pump disposed externally from the handset, wherein the handset include a first fluid line and a second fluid line, the first pump drawing fluid, with suction, from the organ through the first fluid line and pushing the fluid towards the second pump, the second pump drawing the fluid from the first pump and pushing the fluid into the second fluid line. The fluid is drawn from the organ by the first pump carrying tissue cut from the organ by the cutting element, the footswitch is selectively operated to activate the first pump and the second pump, the one or more control elements controlling the operation of the first and the second pumps according to the selected parameters. The first and the second pumps are housed in the footswitch which further includes a motor that is coupled to a gear box and clutch component via a flexible drive shaft, the gear box and clutch component driving the cutting element and the first and the second pumps, the one or more control elements controlling the motor to drive the cutting element and the first and the second pumps according to selected parameters. In an embodiment, a filtration system is disposed externally from the handset and operatively between the first and the second pumps such that the filtration system is configured to filter the fluid sucked from the organ by the first pump, the first pump pushing the fluid through the filtration system and the second pump pulling the filter fluid from the filtration system and pushing the filter fluid into the second fluid line, the second fluid line delivering the filtered fluid to the organ.

In an embodiment, a tissue resecting system, comprising: a handset including: a disposable portion including a pump, a first fluid line, and a second fluid line, the pump drawing fluid, with suction, from an organ through the first fluid line and moving the fluid into the second fluid line for further processing; and a reusable portion that is detachably coupled to the disposable portion to define a single housing for the handset, the reusable portion including one or more drive components that drive the pump; and a cutting element that extends from the handset to cut tissue from the organ, wherein the fluid drawn from the organ by the pump carries tissue cut from the organ by the cutting element. The disposable portion includes a filtration system that filters the fluid from the organ, the pump moving the fluid through the filtration system and into the second fluid line, the second fluid line delivering the filtered fluid to the organ. In alternate embodiments, the second fluid line delivers the fluid to an external receptacle. The one or more drive components in the reusable portion include a motor and drive the cutting element. In an embodiment, the one or more drive components drive the shaft to cause a cutting action with the cutting element and the one or more drive components may include a gearbox and clutch component that divides drive between the pump and the cutting element.

In some embodiments, the system further comprises an endoscope that is configured to be inserted into the organ and to guide the cutting element into the organ, the endoscope including an inflow passageway that is configured to extend into the organ, the passageway being coupled to the second fluid line, the passageway delivering the filtered fluid to the organ. In an embodiment, the reusable portion includes a battery that powers the motor and a cable that electrically couples the motor to an external power source. In an embodiment, the handset includes a control element that is configured to be selectively operated by a user to cause the one or more drive components to engage the cutting element to cause a cutting action, while the one or more drive components continue to drive the pump. In an embodiment, the system further comprises a shaft that extends from the handset and into the endoscope, the cutting element being disposed at an end of the shaft, which comprises an outflow passageway that extends from an opening at the cutting element and into the handset, the outflow passageway being coupled to the first fluid line, the pump drawing the fluid from the organ through the opening and into the outflow passageway via the first fluid line.

In another embodiment, a tissue resecting system, comprising: a handset including a disposable housing including a pump, a first fluid line, a second fluid line, and one or more drive components that drive the pump, the pump drawing fluid, with suction, from an organ through the first fluid line and moving the fluid into the second fluid line for further processing; and a cutting element that extends from the handset to cut tissue from the organ, wherein the fluid drawn from the organ by the pump carries tissue cut from the organ by the cutting element. In an embodiment, the housing includes a filtration system that filters the fluid from the organ, the pump pumping the fluid through the filtration system and into the second fluid line, the second fluid line delivering the filtered fluid to the organ. The system may further comprise an endoscope that is configured to be inserted into the organ and to guide the cutting element into the organ, the endoscope including an inflow passageway that is configured to extend into the organ, the passageway being coupled to the second fluid line, the passageway delivering the filtered fluid to the organ. In an embodiment, the housing comprises a plurality of sections and includes a disposable battery that powers the motor, and the one or more drive components drive the cutting element. In an embodiment, the housing includes a first section and a second section, the first section including the pump, the first fluid line, and the second fluid line, and the second section including the one or more drive components.

In some the one or more drive components include a gear box and clutch component that divides drive between the pump and the cutting element, and the handset includes a control element that is configured to be selectively operated by a user to cause the one or more drive components to engage the cutting element to cause a cutting action, while the one or more drive components continue to drive the pump. In some example, the second fluid line delivers the fluid to an external receptacle. In an embodiment, the system further comprising an endoscope that is configured to be inserted into the organ and to guide the cutting element into the organ and a shaft that extends from the handset and into the endoscope, the cutting element being disposed at an end of the shaft, wherein the shaft includes an outflow passageway that extends from an opening at the cutting element and into the housing, the outflow passageway being coupled to the first fluid line, the pump drawing the fluid from the organ through the opening and into the outflow passageway via the first fluid line, wherein the one or more drive components drive the shaft to cause a cutting action with the cutting element.

According to aspects of the present disclosure, the implementations provide tissue-resecting systems that include footswitches that compactly integrate components for extracting fluid/tissue from an organ. In some implementations, the footswitches include one or more control elements and a motor to drive the pump and the cutting element of a resector according to selected parameters. In other implementations, the footswitches include the pump and the filtration system in addition to the one or more control elements and the motor. The footswitches may include a disposable portion that allows components that contact the fluid/tissue (e.g., the pump, the filtration system, etc.) to be easily disposed, thereby promoting hygienic use of the tissue resecting system. Meanwhile, the footswitches may include a reusable portion that allows other components (e.g., drive components like the motor While the present disclosure has been described with reference to one or more particular implementations, those skilled in the art will recognize that many changes may be made thereto without departing from the spirit and scope of the present disclosure. Each of these implementations and obvious variations thereof is contemplated as falling within the spirit and scope of the disclosure.

What is claimed is:

1. A tissue resecting system, comprising:
   a first portion, including:
      a body defining a fluid path, a first section of the fluid path extending through the body;
      a rotating hub rotatably disposed within the body, the rotating hub defining a second section of the fluid path in fluid communication with the first section of the fluid path;
      a seal disposed on the rotating hub; and
      an elongated assembly extending distally from the body, the elongated assembly including a shaft and a cutting element disposed within the shaft, the cutting element operably coupled to the rotating hub, wherein an internal flow channel extends longitudinally through the elongated assembly and fluidly communicates with the second section of the fluid path, thereby establishing fluid communication from the internal flow channel to the first section of the fluid path;
   a second portion configured to detachably couple to the first portion, the second portion including:
      a case detachably coupled to the body of the first portion, the case defining an internal volume; and
      an electric motor partially disposed within the internal volume of the case, the electric motor defining a hub drive shaft that protrudes through the case of the second portion, the hub drive shaft configured to extend into direct engagement with the rotating hub when the case is coupled to the body of the first portion to enable actuation of the cutting element with the electric motor, wherein the seal fluidly isolates the fluid path from the hub drive shaft when the case is coupled to the body;
   an endoscope configured to be inserted into an organ, the endoscope including a working channel defining an inflow passageway, wherein the elongated assembly of the first portion is configured to telescope through the working channel;
   a pump fluidly coupled to the fluid path, the internal flow channel, and the inflow passageway of the endoscope, wherein the pump is configured to draw fluid and tissue through the internal flow channel and the fluid path; and
   a filter fluidly coupled between the internal flow channel and the inflow passageway, the filter configured to remove tissue from fluid.

2. The tissue resecting system of claim 1, wherein the second portion further includes a heat sink thermally coupled to the electric motor.

3. The tissue resecting system of claim 1, further comprising a cable configured to electrically couple the electric motor with a power source.

4. The tissue resecting system of claim 1, wherein the second portion further includes a battery that powers the electric motor, the battery disposed within the internal volume.

5. The tissue resecting system of claim 1, further comprising a control switch configured to activate the electric motor to drive the cutting element.

6. The tissue resecting system of claim 1, wherein the case of the second portion is detachably coupled to the body of the first portion via at least one of: threaded engagement; snap-fit; frictional engagement; pins; or fasteners.

7. A tissue resecting system, comprising:
a first portion, including:
a body defining a central axis and a fluid path that extends through the body, at least a portion of the fluid path spaced-apart from the central axis on a first side of the central axis;
an elongated assembly extending distally from the body, the elongated assembly including a shaft and a cutting element disposed within the shaft, the elongated assembly defining an internal flow channel extending longitudinally therethrough in fluid communication with the fluid path of the body;
a rotating hub rotatably disposed within the body, the rotating hub coupled to the cutting element and disposed in fluid communication with both the internal flow channel of the elongated assembly and the fluid path of the body, wherein the internal inflow channel and the rotating hub are spaced-apart from the central axis on a second, opposite side of the central axis; and
a seal disposed within the body; and
a second portion configured to detachably couple to the first portion, the second portion including:
a case detachably coupled to the body of the first portion, the case defining an internal volume; and
at least one drive component partially disposed within the internal volume of the case, the at least one drive component including a hub drive shaft that protrudes through the case of the second portion, the hub drive shaft configured to directly engage the rotating hub when the case is coupled to the body of the first portion to enable actuation of the cutting element with the at least one drive component, wherein, when the case is coupled to the body, the at least one drive component is spaced-apart from the central axis on the second, opposite side of the central axis, and
wherein the seal fluidly isolates the fluid path from the hub drive shaft when the case is coupled to the body.

8. The tissue resecting system of claim 7, further comprising:
a pump fluidly coupled to the fluid path and the internal flow channel, the pump configured to draw fluid and tissue through the internal flow channel and the fluid path.

9. The tissue resecting system of claim 7, further comprising:
an endoscope configured to be inserted into an organ, the endoscope including a working channel defining an inflow passageway, wherein the elongated assembly of the first portion is configured to telescope through the working channel.

10. The tissue resecting system of claim 9, further comprising:
a pump fluidly coupled to the fluid path, the internal flow channel, and the inflow passageway of the endoscope; and
a filter fluidly coupled between the internal flow channel and the inflow passageway, the filter configured to remove tissue from fluid,
wherein the pump is configured to draw fluid and tissue through the internal flow channel and the fluid path.

11. The tissue resecting system of claim 7, wherein one of the at least one drive components is powered.

12. The tissue resecting system according to claim 11, further comprising a cable that electrically couples the powered drive component of the at least one drive components to a power source.

13. The tissue resecting system of claim 11, further comprising a battery disposed within the internal volume, the battery configured to power the powered drive component of the at least one drive components.

14. The tissue resecting system of claim 11, further comprising a control switch configured to activate the powered drive component of the at least one drive components to drive the cutting element.

* * * * *